United States Patent
McClure et al.

(10) Patent No.: US 7,157,466 B2
(45) Date of Patent: Jan. 2, 2007

(54) QUINAZOLINE DITOSYLATE SALT COMPOUNDS

(75) Inventors: Michael Scott McClure, Durham, NC (US); Martin Howard Osterhout, Durham, NC (US); Frank Roschangar, Glen Allen, VA (US); Mark Joseph Sacchetti, Foster City, CA (US)

(73) Assignee: SmithKline Beecham (Cork) Limited (IE)

( * ) Notice: Subject to any disclaimer, the term of this patent is extended or adjusted under 35 U.S.C. 154(b) by 144 days.

(21) Appl. No.: 10/311,678

(22) PCT Filed: Jun. 28, 2001

(86) PCT No.: PCT/US01/20706

§ 371 (c)(1), (2), (4) Date: Mar. 31, 2003

(87) PCT Pub. No.: WO02/02552

PCT Pub. Date: Jan. 10, 2002

(65) Prior Publication Data

US 2003/0220354 A1    Nov. 27, 2003

Related U.S. Application Data

(60) Provisional application No. 60/271,845, filed on Feb. 27, 2001, provisional application No. 60/215,508, filed on Jun. 30, 2000.

(51) Int. Cl.
C07D 405/04    (2006.01)
A61K 31/517    (2006.01)
C07D 417/04    (2006.01)

(52) U.S. Cl. ............... 514/264.11; 514/266.2; 514/266.24; 544/279; 544/284; 544/293

(58) Field of Classification Search ............... 544/279, 544/284, 293; 514/266.2, 266.24, 264.11
See application file for complete search history.

(56) References Cited

U.S. PATENT DOCUMENTS

| | | | |
|---|---|---|---|
| 6,169,091 B1 | 1/2001 | Cockerill et al. | 514/258 |
| 6,174,889 B1 | 1/2001 | Cockerill et al. | 514/258 |
| 6,207,669 B1 | 3/2001 | Cockerill et al. | 514/258 |
| 6,391,874 B1 | 5/2002 | Cockerill et al. | 514/233.5 |
| 6,713,485 B1 | 3/2004 | Carter et al. | 514/266.24 |
| 6,723,726 B1 | 4/2004 | Cockerill et al. | 514/258 |
| 6,727,256 B1 | 4/2004 | Carter et al. | 514/258 |

FOREIGN PATENT DOCUMENTS

| | | |
|---|---|---|
| WO | 98/02437 | 1/1998 |
| WO | 99/35146 | 7/1999 |

OTHER PUBLICATIONS

Simone, Oncology: Introduction, Cecil Textbook of Medicine, 20th Edition, vol. 1, pp. 1004-1010, 1996.*
Traxler, Protein Tyrosine Kinase Inhibitors in cancer treatment, Exp. Opin. Ther. Patents, 7(6):571-588, 1997.*
Starling et al., "Synthesis of 2-Substituted Furanonaphthoquinones Using Directed Metalation and Cross Coupling Reactions," *Synthetic Communications*, 28(6), 1998, pp. 1013-1030.
Hanefield et al., "Synthese von Retinoiden mit Aryltetrahydroanthraceunstruktur," *Liebigs Ann. Chem.*, 1994, pp. 59-64.
Bracher et al., "Synthese von 1-Aryl- und 1-Alkeyl-β-carbolinen durch Palladium-katalysierte Kupplungsreaktionen," *Liebigs Ann. Chem.*, 1992, pp. 1315-1319.
Florentin et al., "N° 364.—Synthese et etude RMN des acides furanneboroniques et formylfuranneboroniques," *Bulletin De La Societe Chimique De France*, 1976, No. 11-12, pp. 1999-2005.
Floretin et al., "Etude des $pK_a$ et de la protodeboronation des acides furanneboroniques," *J. Heterocyclic Chem.*, 13, 1976, pp. 1265-1272.

* cited by examiner

*Primary Examiner*—Deepak Rao
(74) *Attorney, Agent, or Firm*—Kathryn I. Coulter; John L. Lemanowicz

(57) ABSTRACT

Ditosylate salts of 4-quinazolineamines are described as well as methods of using the same in the treatment of disorde4rs characterized by aberrant erbB family PTK activity.

10 Claims, 5 Drawing Sheets

QUINAZOLINE DITOSYLATE SALT COMPOUNDS

This application is filed pursuant to 35 U.S.C. § 371 as a U.S. National Phase Application of International Application No. PCT/US01/20706 filed Jun. 28, 2001, which claims priority from 60/215,508 filed Jun. 30, 2000 and 60/271,845 filed Feb. 27, 2001

FIELD OF THE INVENTION

The present invention relates to quinazoline compounds, anhydrate and hydrate ditosylate salts thereof, as well as use and preparation of the same. In particular, the invention relates to ditosylate salts of 4-quinazolineamines. These compounds are inhibitors of various protein tyrosine kinases (PTKs) of the erbB family and consequently are useful in the treatment of disorders mediated by aberrant activity of such kinases.

PRIOR ART BACKGROUND OF THE INVENTION

PTKs catalyze the phosphorylation of specific tyrosyl residues in various proteins involved in the regulation of cell growth and differentiation. (A. F. Wilks, Progress in Growth Factor Research, 1990, 2, 97–111; S. A. Courtneidge, Dev. Supp.I, 1993, 57–64; J. A. Cooper, Semin. Cell Biol., 1994, 5(6), 377–387; R. F. Paulson, Semin. Immunol., 1995, 7(4), 267–277; A. C. Chan, Curr. Opin. Immunol., 1996, 8(3), 394–401). Inappropriate or uncontrolled activation of many PTKs, i.e. aberrant PTK activity, for example by overexpression or mutation, has been shown to result in uncontrolled cell growth.

Aberrant protein tyrosine kinase (PTK) activity has been implicated in a variety of disorders including psoriasis, rheumatoid arthritis, bronchitis, as well as cancer. Development of effective treatments for such disorders is a constant and ongoing enterprise in the medical field. The erbB family of PTKs, which includes c-erbB-2, EGFr, and erbB-4, is one group of PTKs that has attracted interest as a therapeutic target. Currently, of special interest, is the role of erbB family PTKs in hyperproliferative disorders, particularly human malignancies. Elevated EGFr activity has, for example, been implicated in non-small cell lung, bladder, and head and neck cancers. Furthermore, increased c-erbB-2 activity has been implicated in breast, ovarian, gastric and pancreatic cancers. Consequently, inhibition of erbB family PTKs should provide a treatment for disorders characterized by aberrant erbB family PTK activity. The biological role of erbB family PTKs and their implication in various disease states is discussed, for instance in U.S. Pat. No. 5,773,476; International Patent Application WO 99/35146; M. C. Hung et al, Seminars in Oncology, 26: 4, Suppl. 12 (August) 1999, 51–59; Ullrich et al, Cell, 61: 203–212, Apr. 20, 1990; Modjtahedi et al, Int'l. J. of Oncology, 13: 335–342, 1998; and J. R. Woodburn, Pharmacol. Ther., 82: 2–3, 241–250, 1999.

International Patent Application PCT/EP99/00048 filed Jan. 8, 1999, and published as WO 99/35146 on Jul. 15, 1999, discusses PTKs including erbB family PTKs. This published application discloses bicyclic heteroaromatic compounds, including N-{3-Chloro-4-[(3-fluorobenzyl) oxy]phenyl}-6-[5-({[2-(methanesulphonyl)ethyl]amino} methyl)-2-furyl]-4-quinazolinamine; (4-(3-Fluoro-benzyloxy)-3-chloro phenyl)-(6-(2-((2-methanesulphonyl-ethylamino)-methyl)-thiazol-4-yl) quinazolin-4-yl)-amine; and (4-(3-Fluoro-benzyloxy)-3-bromophenyl)-(6-(5-((2-methane sulphonyl-ethylamino)-methyl)-furan-2-yl)quinazolin-4-yl)-amine as well as hydrochloride salts thereof. These compounds show inhibition activity against erbB family PTKs. However, problems exist with the di-HCl salt in that it sorbs very large amounts of water at the humidities to which it might be exposed (e.g., 20–75% relative humidity (RH)) if utilized in a medicament. As a result, suitability of the compound as a medicament could be compromised unless special handling and storage procedures were instituted.

The present inventors have now identified novel ditosylate salts of 4-quinazolineamines, which are suitable as erbB family PTK inhibitors. These ditosylate salts have moisture sorption properties superior to the di-HCl salts of 4-quinazoline amines disclosed in the art. Furthermore, the compounds may be prepared in crystal form and therefore have enhanced physical stability. That is, the ditosylate salts of the present invention sorb much lower amounts of water when exposed to a broad range of humidities and can be prepared in a physically stable crystal form, thus enhancing its suitability as a medicament.

DISCLOSURE OF THE INVENTION

In a first aspect of the present invention, there is provided a compound of formula (I),

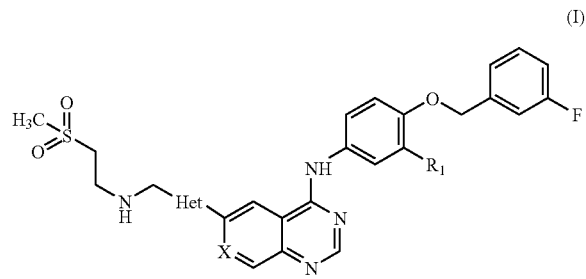

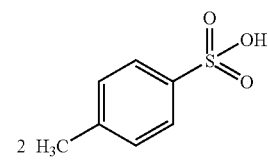

and anhydrate or hydrate forms thereof, wherein $R_1$ is Cl or Br; X is CH, N, or CF; and Het is thiazole or furan.

In a second aspect of the present invention, there is provided a compound of formula (II),

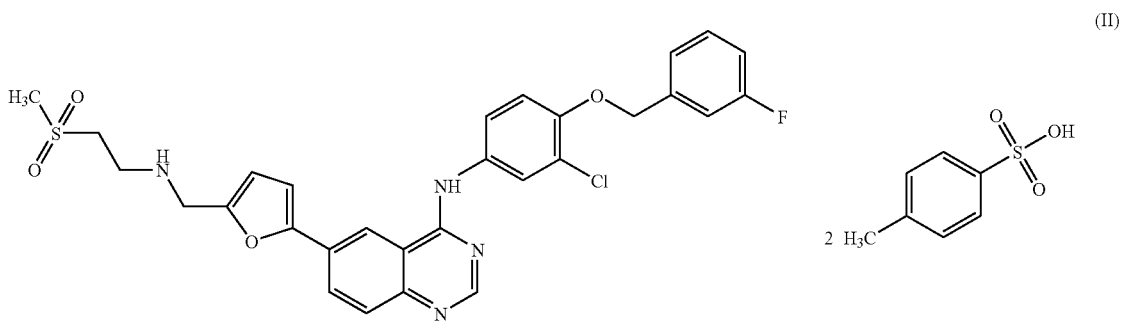

and anhydrate or hydrate forms thereof.

In a third aspect of the present invention, there is provided a pharmaceutical composition including a therapeutically effective amount of a compound of formula (I) and anhydrate or hydrate forms thereof.

In a fourth aspect of the present invention, there is provided a pharmaceutical composition including a therapeutically effective amount of a compound of formula (II) and anhydrate or hydrate forms thereof.

In a fifth aspect of the present invention, there is provided a method of treating a disorder in a mammal, said disorder being characterized by aberrant activity of at least one erbB family PTK, including: administering to said mammal a therapeutically effective amount of a compound of formula (I), or anhydrate or hydrate forms thereof.

In a sixth aspect of the present invention, there is provided a method of treating a disorder mediated by aberrant protein tyrosine kinase activity in a mammal, including: administering to said mammal an amount of a compound of formula (I) or anhydrate or hydrate form thereof, effective to inhibit at least one erbB family protein.

In a seventh aspect of the present invention, there is provided a compound of formula (I), or anhydrate or hydrate forms thereof, for use in therapy.

In an eight aspect of the present invention, there is provided use of a compound of formula (I), and anhydrate or hydrate forms thereof, in the preparation of a medicament for use in the treatment of a disorder characterized by aberrant erbB family PTK activity.

DETAILED DESCRIPTION OF THE INVENTION

Figure 1:
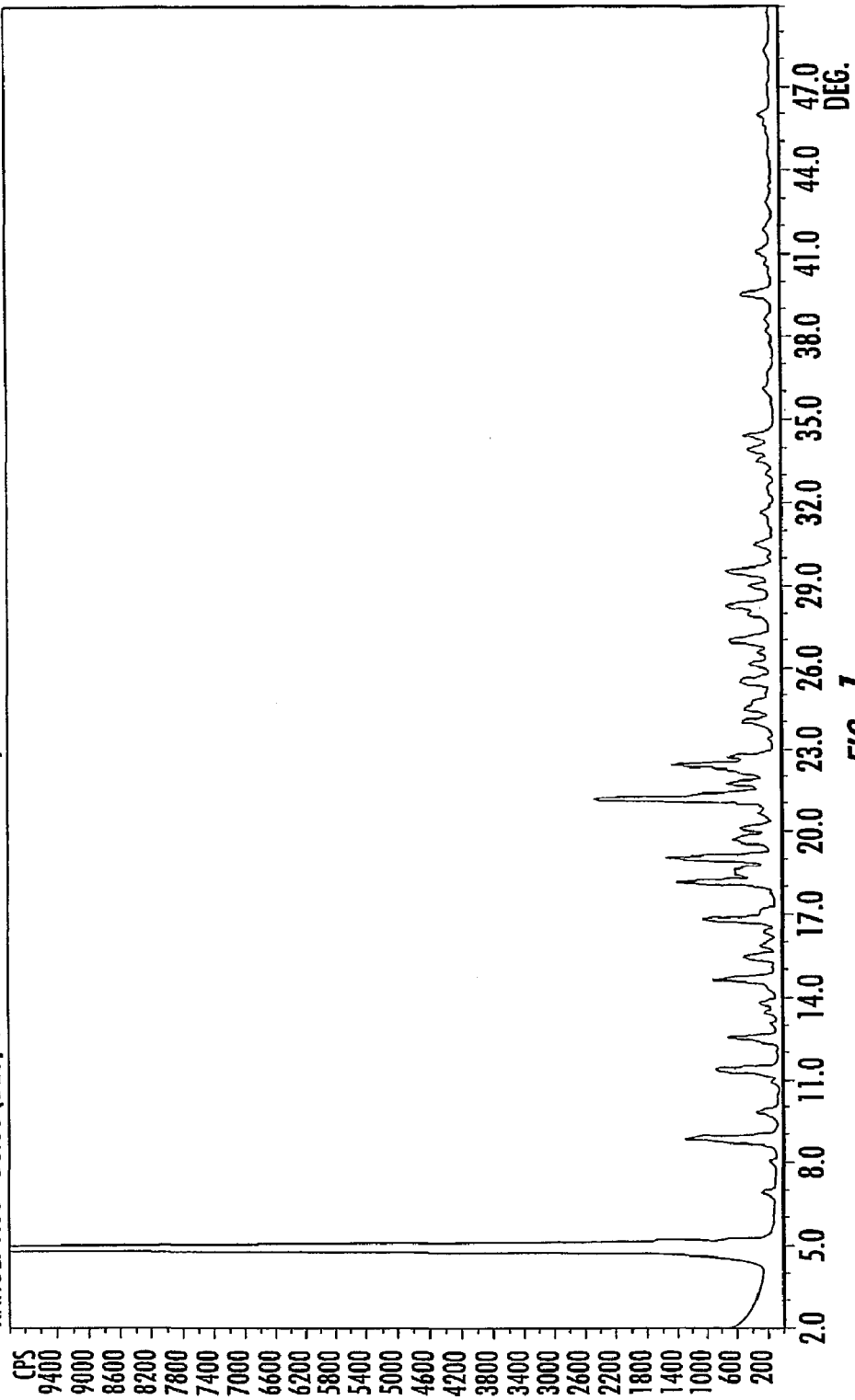
FIG. 1 depicts the powder X-ray diffraction pattern of N-{3-Chloro-4-[(3-fluorobenzyl) oxy]phenyl}-6-[5-({[2-(methanesulphonyl)ethyl] amino}methyl)-2-furyl]-4-quinazolinamine ditosylate anhydrate.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" refers to a straight or branched chain hydrocarbon having from one to twelve carbon atoms. Examples of "alkyl" as used herein include, but are not limited to, methyl, ethyl, ispropyl, n-propyl, n-butyl, n-pentyl, isobutyl, and the like.

It is to be understood that the following embodiments refer to compounds within the scope of formula (I) andformula (II), (III), or (IV) as defined herein unless specifically limited by the definition of each formula or specifically limited otherwise. It is also understood that the embodiments of the present invention, including uses, compositions, and processes for making, described herein, while being described with regard to compounds of formula (I) are applicable to compounds of formulae (II), (III), and (IV).

As recited above, the compounds of the present invention include compounds of Formula (I) or anhydrate or hydrate forms thereof, where $R_1$ is Cl or Br; X is CH, N, or CF; and Het is furan or thiazole.

The side chain $CH_3SO_2CH_2CH_2NHCH_2$ of the compounds of formula (I) may be linked to any suitable position of the group Het. Similarly, the phenyl group of the quinazoline core may be linked to any suitable position of the group Het.

In one embodiment, $R_1$ is Cl; X is CH; and Het is furan; preferably a compound of Formula (II) and anhydrate or hydrate forms thereof.

The compound of formula (II) has the chemical name N-{3-Chloro-4-[(3-fluorobenzyl) oxy]phenyl}-6-[5-({[2-(methanesulphonyl) ethyl]amino}methyl)-2-furyl]-4-quinazolinamine ditosylate.

In one embodiment, the compound is the monohydrate form of the compound of formula II. In one embodiment, the monohydrate form has a water content of 1.5 to 3.0, preferably 1.7 to 2.5, more preferably 1.8 to 2.2 percent by weight.

In another embodiment, the compound is the anhydrate form of the compound of formula (II). In one embodiment, the anhydrate form has a water content of less than 1.5, preferably less than 1.0, more preferably less than 0.5 percent by weight.

In a further embodiment, the compound is a compound of formula (II) characterized by a powder x-ray diffraction pattern including the peaks of Table I.

TABLE I

| Two theta (deg)* | d-spacing (angstroms) |
|---|---|
| 4.8 | 18 |
| 8.7 | 10 |
| 18.0 | 4.9 |
| 18.9 | 4.7 |
| 21.0 | 4.2 |
| 22.3 | 4.0 |

*Based on Cu Kα radiation. Kα2 was removed prior to peak location

In another embodiment, the compound is a compound of formula (II) characterized by a powder x-ray diffraction pattern including the peaks of Table II.

TABLE II

| Two theta (deg)* | d-spacing (angstroms) |
|---|---|
| 6.6 | 13 |
| 8.3 | 10 |
| 11.5 | 7.7 |
| 18.1 | 4.9 |
| 21.1 | 4.2 |

*Based on Cu Kα radiation. Kα2 was removed prior to peak location

In an alternative embodiment, $R_1$ is Cl; X is CH; and Het is thiazole; preferably a compound of formula (III) and anhydrate or hydrate forms thereof.

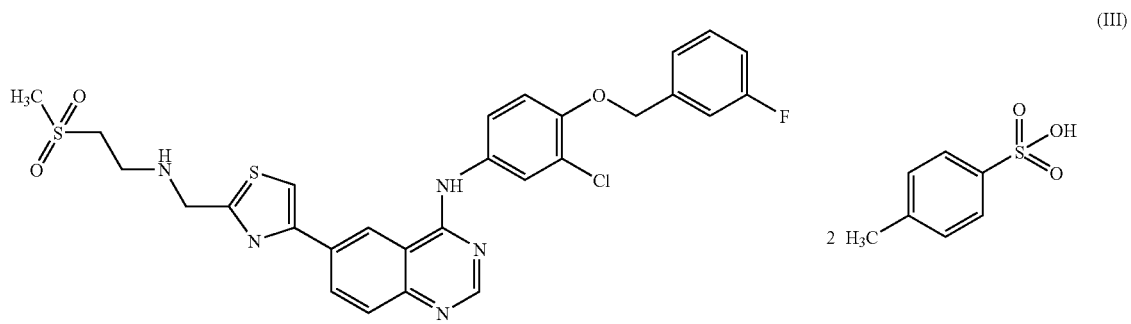

(III)

The compound of formula III is (4(3-Fluoro-benzyloxy)-3-chlorophenyl)-(6-(2-((2-methanesulphonyl-ethylamino)-methyl)-thiazol-4-yl)quinazolin-4-yl)-amine ditosylate.

In a further alternative embodiment, $R_1$ is Br; X is CH; and Het is furan; preferably, a compound of formula (IV) and anhydrate or hydrate forms thereof.

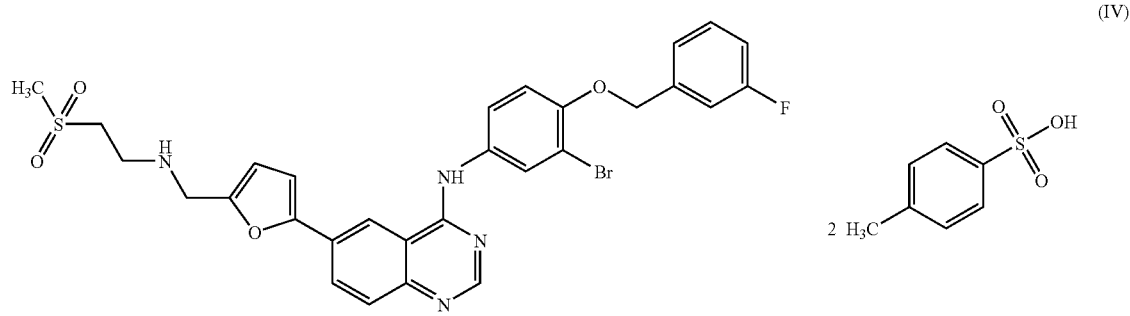

The compound of formula (IV) is (4-(3-Fluoro-benzyloxy)-3-bromophenyl)-(6-(5-((2-methanesulphonyl-ethylamino)-methyl)-furan-2-yl)quinazolin-4-yl)-amine ditosylate.

The compounds of formula (I), including the compounds of formulae (II), (III), and (IV), include within their scope substantially pure anhydrate or hydrate forms, as well as mixtures of hydrate and anhydrate forms. It is also understood, that such compounds include crystalline or amorphous forms and mixtures of crystalline and amorphous forms.

While it is possible that, for use in therapy, therapeutically effective amounts of a compound of formula (I), as well as anhydrate or hydrate forms thereof, may be administered as the raw chemical, it is possible to present the active ingredient as a pharmaceutical composition. Accordingly, the invention further provides pharmaceutical compositions, which include therapeutically effective amounts of compounds of the formula (I) and anhydrate or hydrate forms thereof, and one or more pharmaceutically acceptable carriers, diluents, or excipients. The compounds of the formula (I) and anhydrate or hydrate forms thereof, are as described above. The carrier(s), diluent(s) or excipient(s) must be acceptable in the sense of being compatible with the other ingredients of the formulation and not deleterious to the recipient thereof. According to another aspect of the invention there is also provided a process for the preparation of a pharmaceutical formulation including admixing a compound of the formula (I), or anhydrate or hydrate forms thereof, with one or more pharmaceutically acceptable carriers, diluents or excipients.

Compounds of formula (I) and anhydrate or hydrate forms thereof may be formulated for administration by any route, and the appropriate route will depend on the disease being treated as well as the subjects to be treated. Suitable pharmaceutical formulations include those for oral, rectal, nasal, topical (including buccal, sub-lingual, and transdermal), vaginal or parenteral (including intramuscular, sub-cutaneous, intravenous, and directly into the affected tissue) administration or in a form suitable for administration by inhalation or insufflation. The formulations may, where appropriate, be conveniently presented in discrete dosage units and may be prepared by any of the methods well know in the pharmacy art.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable. binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and anhydrate or hydrate forms thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and anhydrate and hydrate forms thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation, through the nasal passage from a container of the powder held close up to the nose. Suitable formulations wherein the carrier is a liquid, for administration as a nasal spray or as nasal drops, include aqueous or oil solutions of the active ingredient Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

Also provided in the present invention, is a method for treating a disorder in a mammal characterized by aberrant activity of at least one erbB family PTK which includes administering a therapeutically effective amount of a compound of formula (I), and anhydrate or hydrate forms thereof, to the mammal. The compounds of formula (I) and anhydrate or hydrate forms thereof are as described above.

The aberrant PTK activity referred to herein is any erbB family PTK activity that deviates from the normal erbB family protein kinase activity expected in a particular mammalian subject. Aberrant erbB family PTK activity may take the form of, for instance, an abnormal increase in activity, or an aberration in the timing and or control of PTK activity. Such aberrant activity may result then, for example, from overexpression or mutation of the protein kinase leading to inappropriate or uncontrolled activation. Furthermore, it is also understood that unwanted PTK activity may reside in an abnormal source, such as a malignancy. That is, the level of PTK activity does not have to be abnormal to be considered aberrant, rather the activity derives from an abnormal source.

The compounds of formula (I) and anhydrate or hydrate forms thereof, are inhibitors of one or more erbB family PTKs and as such have utility in the treatment of disorders in mammals which are characterized by aberrant PTK activity, particularly humans. In one embodiment of the present invention, the disorder treated is characterized by at least one erbB family PTK, selected from EGFr, c-erb-B2 and c-erb-B4, exhibiting aberrant activity. In another embodiment, the disorder treated is characterized by at least two erbB family PTKs, selected from EGFr, c-erb-B2 and c-erb-B4, exhibiting aberrant activity. In one embodiment of the treatment method, the compounds of formula (I) or anhydrate or hydrate forms thereof inhibit at least one erbB family PTK, selected from EGFr, c-erb-B2 and c-erb-B4. In another embodiment of the treatment method, the compounds of formula I or anhydrate or hydrate forms thereof inhibit at least two erbB family PTKs selected from EGFr, c-erb-B2 and c-erb-B4.

Accordingly, also provided is a method of treating a disorder mediated by aberrant protein tyrosine kinase activity in a mammal, including: administering to said mammal an amount of a compound of formula (I) or anhydrate or hydrate form thereof, effective to inhibit at least one erbB family protein. In one embodiment, the method includes administering an amount of a compound of formula (I) or anhydrate or hydrate form thereof, effective to inhibit at least two erbB family proteins.

The disorders referred to may be any disorder which is characterized by aberrant PTK activity. As recited above such disorders include, but are not limited to, cancer and psoriasis. In a preferred embodiment, the disorder is cancer. In a more preferred embodiment, the cancer is non-small cell lung, bladder, prostate, brain, head and neck, breast, ovarian, gastric, colorectal, or pancreatic cancers.

A therapeutically effective amount of a compound of formula (I) and anhydrate or hydrate forms thereof will depend on a number of factors including, but not limited to, the age and weight of the mammal, the precise disorder requiring treatment and its severity, the nature of the formulation, and the route of administration, and will ultimately be at the discretion of the attendant physcian or veternarian. Typically, the compounds of formula (I) and anhydrate or hydrate forms thereof will be given for treatment in the range of 0.1 to 100 mg/kg body weight of recipient (mammal) per day and more usually in the range of 1 to 10 mg/kg body weight per day. Acceptable daily dosages, may be from about 0.1 to about 1000 mg/day, and preferably from about 0.1 to about 100 mg/day.

The compounds of formula (I) and anhydrate or hydrate forms thereof, described above, are useful in therapy and in the preparation of medicaments for treating a disorder in a mammal, which is characterized by aberrant activity of at least one erbB family PTK. In one embodiment of the present invention, the medicament prepared is useful in treating a disorder characterized by at least one erbB family PTK, selected from EGFr, c-erb-B2 and c-erb-B4, exhibiting aberrant activity. In another embodiment, the medicament prepared is useful in treating a disorder characterized by at least two erbB family PTKs, selected from EGFr, c-erb-B2 and c-erb-B4, exhibiting aberrant activity. In one embodiment of the use, the compounds of formula (I) or anhydrate or hydrate forms thereof, which are used to form the medicament, inhibit at least one erbB family PTK, selected from EGFr, c-erb-B2 and c-erb-B4. In another embodiment of the use, the compounds of formula (I) or anhydrate or hydrate forms thereof, which are used to form the medicament, inhibit at least two erbB family PTKs selected from EGFr, c-erb-B2 and c-erb-B4, The disorders treated are as described above.

The free base and HCl salts of the compounds of Formulae (I), (II), (III), and (IV), may be prepared according to the procedures of International Patent Application No. PCT/EP99100048, filed Jan. 8, 1999, and published as WO 99/35146 on Jul. 15, 1999, referred to above. A schematic of such procedures is presented in Scheme A following. The specific page references given are to WO 99/35146. The free base of the compound of formula II is used as an example of the general scheme.

Scheme A

Procedure A - Reaction of an amine with a bicyclic species containing a 4- chloropyrimidine ring
(p. 55, lines 21–33, p. 69, lines 30–34 and p. 74, line 35 - p. 75,

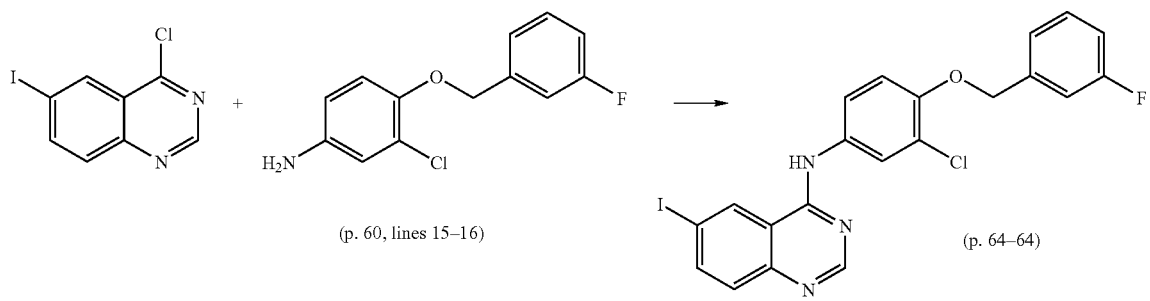

(p. 60, lines 15–16)    (p. 64–64)

Procedure B - Reaction of Procedure A product with heteroaryl tin reagent (p. 55, line 33 - p. 56, line 9)

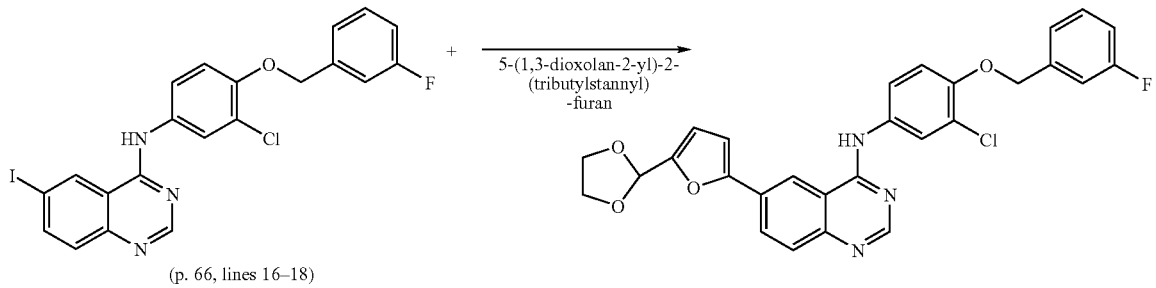

(p. 66, lines 16–18)

Procedure C - Removal of a 1,3-dioxolan-2yl protecting group to liberate an aldehyde (P. 56, lines 11–18)

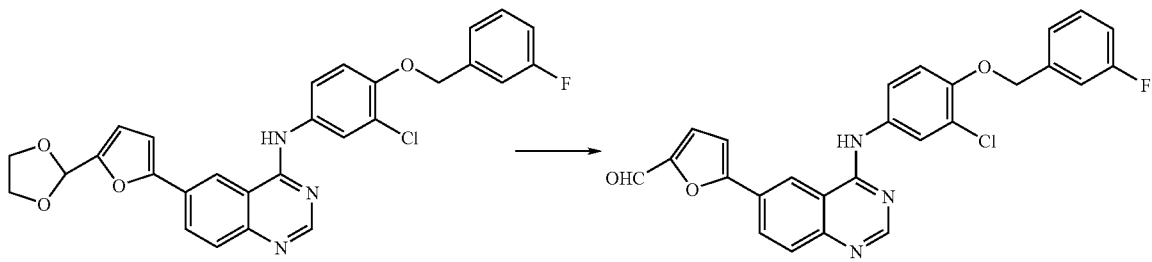

Procedure D - Reaction of an aldehyde with an amine by reductive amination (p. 56, lines 20–32; Example 29 - p. 100, lines 18–29)

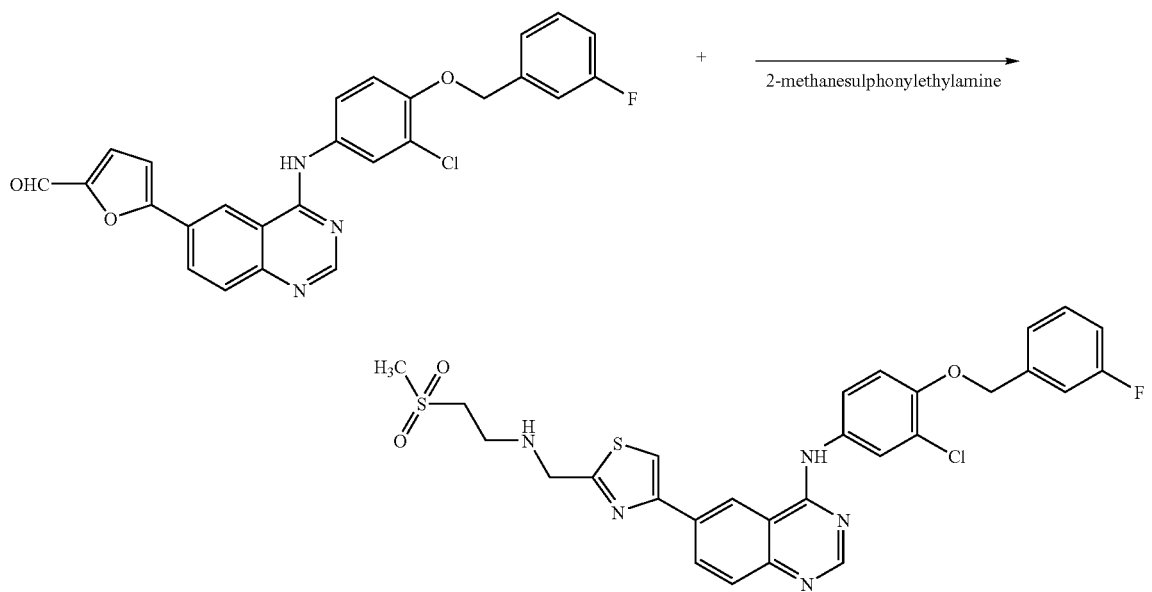

The compound of formula (II), i.e., N-{3-Chloro-4-[(3-fluorobenzyl) oxy]phenyl}-6-[5-({[2-(methanesulphonyl) ethyl]amino}methyl)-2-furyl]-4-quinazolinamine ditosylate has been prepared in two distinct forms, an anhydrate form (Formula II' in Scheme B) and a monohydrate form (Formula II" in Scheme B). The relationship of these forms is illustrated in Scheme B below. The anhydrate form of N-{3-Chloro-4-[(3-fluorobenzyl) oxy]phenyl}-6-[5-({[2-(methanesulphonyl)ethyl]amino}methyl)-2-furyl]-4-quinazolinamine ditosylate may be prepared by (a) reacting the tosylate salt of 5-(4-[3-chloro-4-(3-fluorobenzyloxy)-anilino]-6-quinazolinyl)-furan-2-carbaldehyde (formula B in Scheme B) with 2-(methylsulfone)ethylamine in tetrahydrofuran in the presence of diisopropyl-ethylamine followed by (b) the introduction of this solution into to a slurry of sodium triacetoxyborohydride in tetrahydrofuran at room temperature, (c) adding 5N sodium hydroxide to adjust the pH to within a range of 10–11, (d) separating the organic tetrahydrofuran phase, and then (e) adding para-toulenesulfonic acid hydrate to the organic phase to provide the ditosylate anhydrate. Interconversion to the monohydrate and back to the anhydrate of the ditosylate salt compounds of the invention is as depicted in Scheme B. The tosylate salt of 5-(4-[3-chloro-4-(3-fluorobenzyloxy)-anilino]-6-quinazolinyl)-furan-2-carbaldehyde is prepared from the HCl salt of the carbaldehyde (Formula A of Scheme B). Preparation of N-{3-Chloro-4-[(3-fluorobenzyl) oxy]phenyl}-6-[5-({[2-(methanesulphonyl)ethyl]amino}methyl)-2-furyl]-4-quinazolinamine ditosylate and the anhydrate and monohydrate forms thereof are utilized as an example. As recognized by those skilled in the art, other compounds of formula I and anhydrate and hydrate forms thereof may be prepared by similar methods.

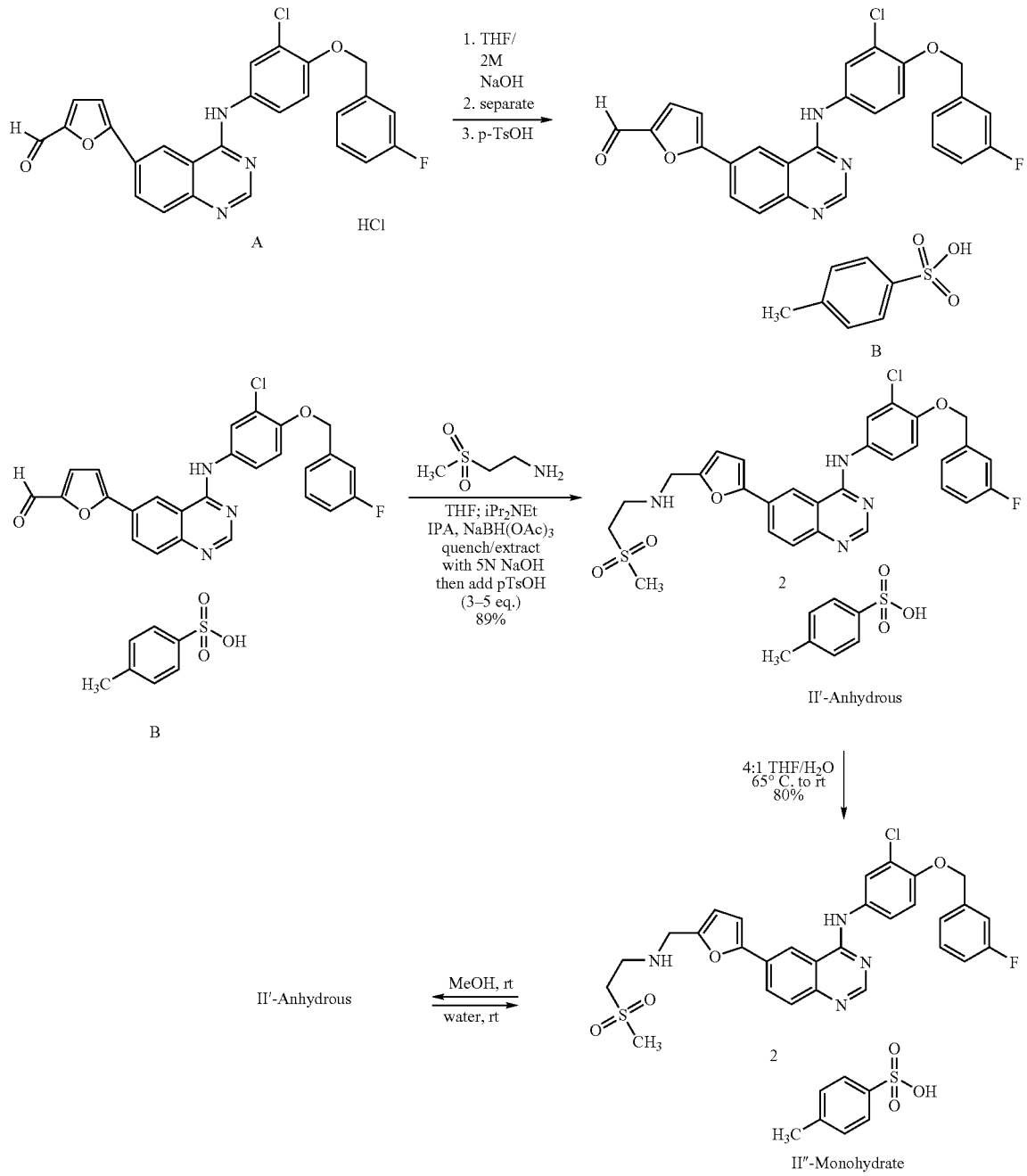

Compound A of Scheme B may be prepared by various synthetic strategies, other that the strategy recited in Scheme A above, utilizing the palladium(O) mediated coupling of quinazoline and substituted furan intermediates.

Scheme C depicts five palladium(O) mediated coupling strategies, to synthesize compound A of Scheme B. Synthesis (1), the prior art method, involves the use of commercially available 5-formyl-2-furylboronic acid in the Suzuki reaction. Synthesis (2) through (5) represent various embodiments of the present invention which include: (2) generation of 5-(diethoxymethyl)-2-furylboronic acid and its in situ use in the Suzuki coupling, (3) generation of 5-formyl-2-furylboronic acid from 2-furaldehyde via in situ protection of the formyl moiety with N,O-dimethylhydroxylamine, and its in situ use in the Suzuki coupling, (4) generation of 5-formyl-2-furylboronic acid from 5-bromo-2-furaldehyde via in situ protection of the formyl moiety with N,O-dimethylhydroxylamine, and its in situ use in the Suzuki coupling, and finally (5) the reverse Suzuki coupling of in situ generated 4-{3-chloro-4-[(3-fluorobenzyl)oxy]anilino}-6-quinazolinylboronic acid (prepared from N-{3-chloro-4-[(3-fluorobenzyl)oxy]phenyl}-6-iodo-4-quinazolinamine) with 5-bromo-2-furaldehyde.

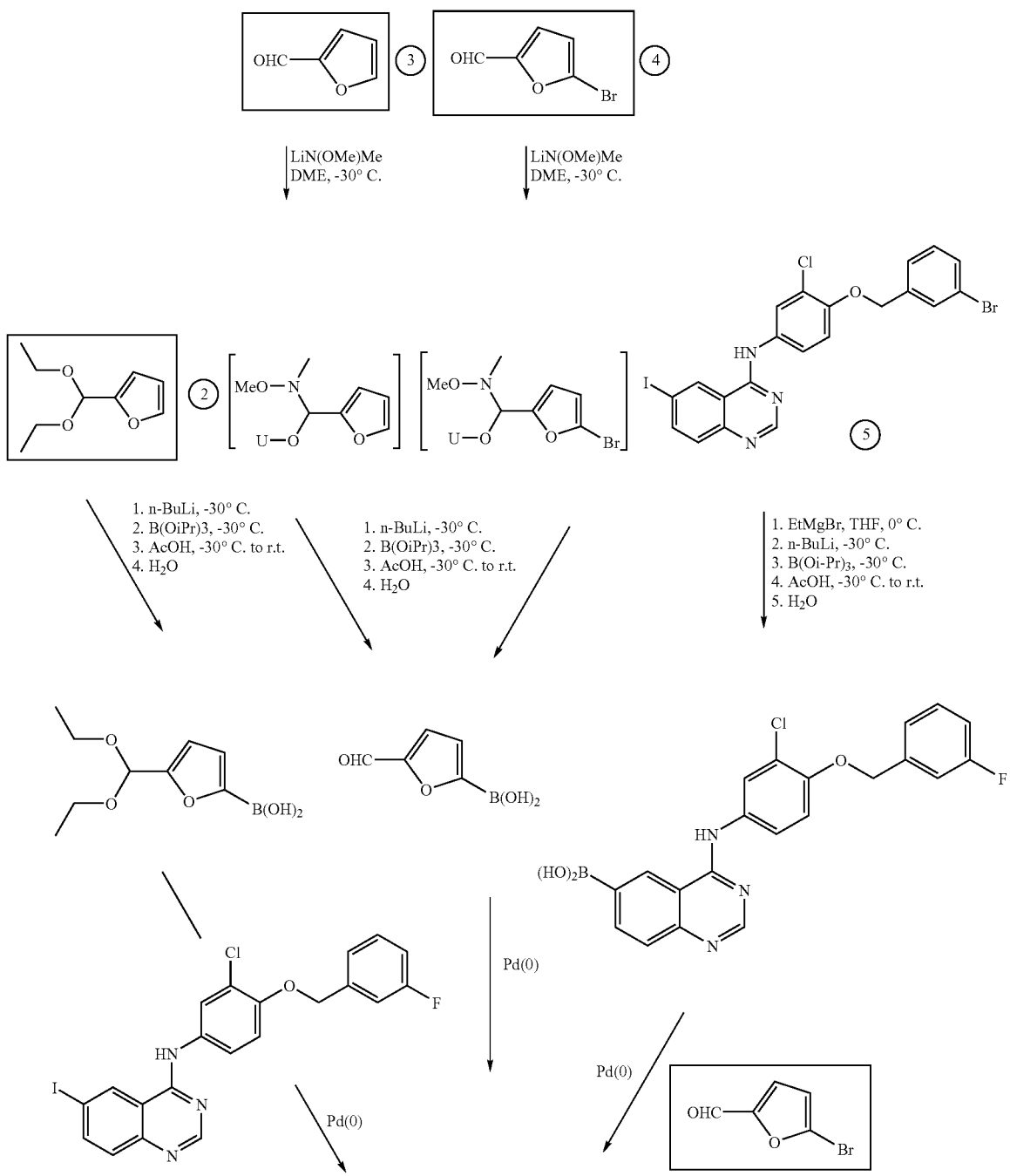

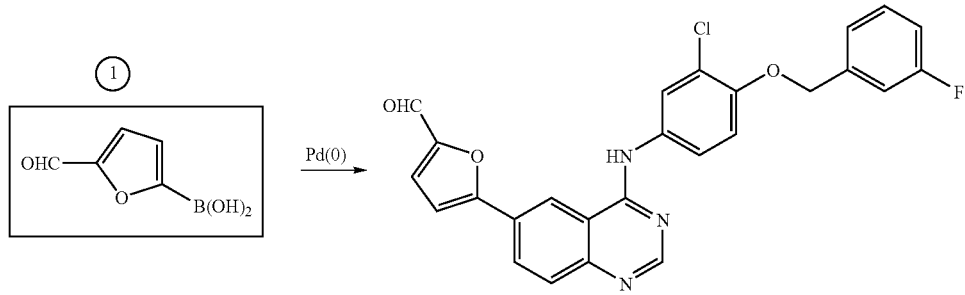

The reactions of Scheme C, are described following with reference to formulae (C), (A), and (B).

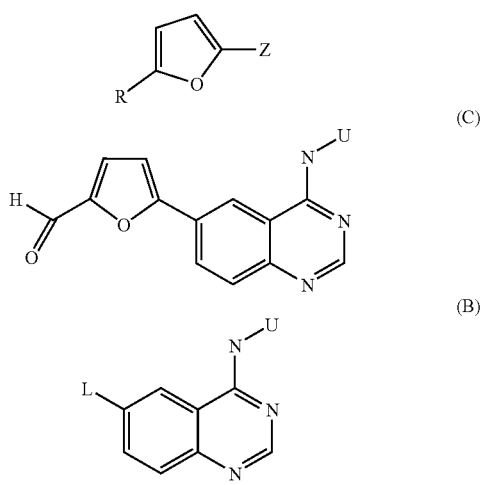

In (1) of Scheme C, the commercially available 5-formyl-2-furylboronic acid, i.e., the compound of formula (A) wherein R is —C(O)H and Z is —B(OH)$_2$, (Frontier Scientific, Inc.; Logan Utah), undergoes catalytic palladium (O)-mediated coupling (*Pure Appl. Chem.* 1994, 66, 213; *Synth. Commun.* 1981, 11, 513) to form the desired compound of Formula (C) in high yields. Specifically, a compound of formula (C) is made by mixing a compound of formula (B), wherein L is iodine or bromine, preferably iodine and U is an organic group as described herein, and 1.0–1.5 molar equivalents of 5-formyl-2-furylboronic acid, in an ethereal solvent such as, but not limited to, diethyl ether, tetrahydrofuran, dioxane, ethylene gylcol diethyl ether also known as 1,2-diethoxyethane and ethylene gylcol dimethyl ether also know as 1,2-dimethoxyethane or DME. A palladium catalyst is then added from a list that includes palladium(II) acetate, palladium(II) chloride, palladium on carbon, dichloro[1,1'-bis(diphenylphosphino)ferrocene]palladium(II), tetrakis(triphenylphosphine) pallladium(O), tris (dibenzylideneacetone)dipalladium(O), trans-dichlorobis (triphenyl phosphine) palladium(II). The preferred catalyst is palladium on carbon. This reaction is then heated to between 25° C. and 120° C. for 1–24 hours and then cooled to ambient temperature and filtered. The solution is then treated with a mineral acid or an organic acid, such as p-toluenesulfonic acid monhydrate, and the compound of formula (C) is isolated in high yields as its mineral acid salt or p-toluenesulfonic acid salt.

Another approach to a compound of formula (C) employs advancing a crude solution of a compound of formula (A) wherein Z is B(OH)$_2$ and R is —C(Q)(T)W where Q and T are O-alkyl, where alkyl is as defined herein and is preferably ethyl, and W is hydrogen, in a palladium(O) mediated biaryl coupling (Suzuki cross coupling with in situ generated boronic acids is described in *J. Org. Chem.* 1996, 61, 9556, and references cited therein) with a compound of formula. (B), wherein L is iodine or bromine and U is an organic group, using "ligand-less" heterogeneous catalysis with palladium on carbon. Such use of "ligand-less" palladium is reported in *Org. Lett.* 1999, 1, 965; *Org. Process Res. Dev.* 1999, 3, 248; and *Tetrahedron Lett.* 1994, 35, 3277. A preferred embodiment of this approach, partially depicted in (2) of Scheme C, provides for (i) the in situ generation of furanyl lithiate, a compound of formula (A), wherein Z is Li and R is —C(Q)(T)W where Q and T are O-alkyl, preferably ethoxy, and W is hydrogen, (ii) subsequent generation of the corresponding boronic acid, wherein Z is B(OH)$_2$ and R is —C(Q)(T)W where Q and T are O-alkyl, preferably ethoxy, and W is hydrogen, and (iii) the palladium(O)-mediated biaryl coupling to construct the desired compound of formula (C). The process utilizes ethereal solvents. These ethereal solvents can include, but are not limited to, diethyl ether, tetrahydrofuran, dioxane, 1,2-diethoxyethane and DME. The preferred solvent is DME. This preferred solvent was observed to offer significant improvements over published procedures (*Synth. Commun.* 1998, 28, 1013) in the formation of 5-formyl-2-furylboronic acid synthesized from 2-furaldehyde diethylacetal. Another suitable precursor to in situ generated 5-formyl-2-furylboronic acid included 2-(2-furyl)-1,3-dioxolane. Advantages of this process include deprotonation of the compound of formula (A), wherein Z is hydrogen and R is —C(Q)(T)W where Q and T are O-alkyl, preferably ethoxy, and W is hydrogen, with alkyl lithiums, preferably n-butyl lithium, at higher temperatures (−20° C. in DME compared to −40° C. in tetrahydrofuran). Subsequent treatment of the compound of formula (A), wherein Z is Li and R is —C(Q)(T)W where Q and T are O-alkyl, preferably ethoxy, and W is hydrogen, with trialkyl borate, preferably triisopropyl borate in DME also provided higher conversion to the borate ester of the compound of formula (A), wherein Z is B(O-isopropyl)$_3$Li and R is —C(Q)(T)W where Q and T are O-alkyl, preferably ethoxy, and W is hydrogen. In preparation for the subsequent Suzuki coupling, the in situ generated borate ester was hydrolyzed to the boronic acid of the compound of formula (A), wherein Z is B(OH)$_2$ and R is —C(Q)(T)W where Q and T are O-alkyl, where alkyl is as defined herein, preferably ethyl, and W is hydrogen by first treating with acetic acid followed by addition with water in that specific order at ambient temperature. It was also observed that the superior process improvements from the use of DME, as compared to tetrahydrofuran, extended to the palladium(O)-mediated biaryl coupling with boronic acid intermediate to give a compound of formula (C). Such process improvements include more consistent yields, shorter reaction times, and enhanced purity profiles.

In another embodiment, compounds of formula (C) can be formed from a palladium(0) mediated biaryl union of 5-formyl-2-furylboronic acid, the compound of formula (A) wherein Z is —B(OH)$_2$, generated in situ and a compound of formula (B), where L is iodine or bromine and U is an organic group (See (3) of Scheme C). This process employs an in situ protection of the aldehyde functionality as an aminal lithiate, (*Synlett* 1992, 615), as in the reaction of, for example, 2-furaldehyde with the lithium anion of a secondary amine chosen from morpholine, N,O-dimethylhydroxylamine, 1-methylpiperizine or N$^1$, N$^1$, N$^2$-trimethyl-1,2-ethanediamine. The preferred amine in this process is N,O-dimethylhydroxylamine. Formation of the amine lithiate is accomplished by treatment of the amine with an alkyl lithium reagent, preferably n-butyl lithium, in an ethereal solvent such as tetrahydrofuran or DME at low temperature. The solution of the amine lithium anion is then mixed with 2-furaldehyde to form the in situ aminal lithiate, a compound of formula (A), wherein Z is hydrogen, R is —C(Q)(T)W where Q is NR'R", wherein R' is O-alkyl, preferably methoxy and R" is an alkyl as defined herein, preferably methyl or R' and R" are independently alkyl as defined herein; T is O—Li and W is H. This solution is then treated with an additional molar equivalent of an alkyl lithium, preferably n-butyl lithium, at low temperature to form the furanyl lithate, a compound of formula (A), wherein Z is Li and R is —C(Q)(T)W where Q is NR'R" where R' is O-alkyl, preferably methoxy and R" is alkyl, preferably methyl or R' and R" are independently alkyl as define herein, T is O—Li and W is H. This solution is then treated at low temperature with a trialkylborate, preferably triisopylborate, to form a compound of formula (A), wherein Z is B(O-isopropyl)$_3$Li, R is —C(Q)(T)W where Q is NRR', where R' can be O-alkyl, preferably methoxy and R" is an alkyl as defined herein, preferably methyl or R' and R" are independently alkyl as defined herein; T is O—Li and W is hydrogen, and hydrolyzed to the 5-formyl-2-furylboronic acid in solution by the addition of either a mineral or organic acid, such as acetic acid. This in situ generated 5-formyl-2-furylboronic acid readily undergoes a palladium(O)-mediated biaryl coupling to form a compound of formula (C).

The process, described in the preceding paragraph, to obtain a compound of formula (C), can also be employed when using a halogen (Z is bromine or iodine) substituted 2-furaldehyde derivatives, preferably 5-bromo-2-formylfuran. That is, a compound of formula (A) where Z is bromine and R is —C(O)H (See (4) of Scheme C).

Alternatively, another synthetic strategy to compounds of formula (C) can be constructed from a palladium(O) mediated biaryl coupling of N-heteroaryl boronic acids, such as a compound of formula (B), wherein L is B(OH)$_2$ and U is an organic group, with 5-halogen-2-formylfuran derivatives, that is a compound of formula (A) where Z is bromine or iodine and R is —C(O)H. (See (5) of Scheme C). A process for making a N-heteroaryl boronic acid intermediate of formula (B) involves the treatment of a compound of formula (B), wherein L is iodine and U is an organic group, with an alkylmagnesium halide reagent, preferably ethylmagnesium bromide. The reaction is performed in an ethereal solvent such as tetrahydrofuran or DME at low temperature. This mixture is then treated with a trialkylborate, preferably triisopropyl borate followed by slow addition of an alkyllithium, preferably n-butyllithium, while maintaining the reaction at low temperature. This is then followed by the addition of a mineral acid or organic acid, preferably acetic acid. This gives an N-heteroaryl boronic acid intermediate of formula (B), wherein L is B(OH)$_2$ and U is an organic group in solution. To this is then added 5-halogen-2-furaldehyde-(halogen is bromine or iodine), preferably 5-bromo-2-furaldehyde, a co-solvent such as N,N-dimethylacetamide, an aqueous base, such as sodium carbonate and a palladium catalyst, such as dichloro[1,1'-bis(diphenylphosphino)ferrocene]palladium(II) dichloromethane adduct. This solution is then heated to a sufficient temperature to provide conversion to the desired compound of formula (C).

A different synthetic strategy for the construction of a compound of formula (C), is to use a Heck-type reaction (*Bull Chem. Soc. Jpn.* 1973, 46, 1220; *Heterocycles* 1990, 31, 1951; *Synthesis* 1984, 488; *J. Org. Chem.* 1985, 50, 5272) to couple 2-furaldehyde, a compound of formula (A) wherein Z is hydrogen and R is —C(O)H, in a regioselective manner with an intermediate of formula B, wherein L is iodine or bromine and U is an organic group. The regioselective palladium catalyzed arylation of 2-furaldehyde, in the 5-position is unprecedented in the chemical literature. Other suitable substitutes for 2-furaldehyde in this process include 2-furaldehyde diethylacetal, 2-(2-furyl)-1,3-dioxolane, 2-furanoic acid and esters of 2-furanoic acid such as methyl 2-furanoate or ethyl 2-furanoate. The process for the synthesis of a compound of formula (C) employing this strategy entails mixing an appropriate solvent, such as N,N-dimethylformamide, N-methylpyrrolidinone, toluene, dimethylacetamide, water, acetonitrile or mixtures thereof, preferably N,N-dimethylformamide, with an organic amine base, such as triethylamine and diisopropylethylamine or an alkali metal carboxylate base, such as sodium carbonate, potassium carbonate, cesium carbonate, calcium carbonate, sodium acetate and potassium acetate, preferably potassium acetate, and 2-furaldehyde. This is then followed by the addition of a trialkyl- or triarylphosphine, such as tri-o-tolylphosphine, triphenylphosphine, tri-tert-butylphosphine, tri-2-furylphosphine, tricyclohexylphosphine, preferably tricyclohexylphosphine. A palladium catalyst is added from a list that includes, but is not limited to, palladium(II) acetate, palladium(II) chloride, palladium on carbon, dichloro[1,1'-bis(diphenylphosphino)ferrocene]palladium(II), tetrakis (triphenylphosphine) palladium(O), tris(dibenzylideneacetone)dipalladium(O), trans-dichlorobis(triphenylphosphine)palladium(II), preferably palladium(II) chloride. This mixture is then heated and a solution of a compound of formula (B), wherein L is iodine or bromine, preferably iodine, is slowly added. This reaction mixture is then heated for 10–20 hours at which point the reaction mixture is cooled to ambient temperature and filtered. Addition of a mineral acid or organic acid, such as p-toluenesulfonic acid, provides an isolated compound of formula (C) as its salt In one embodiment of the present invention, there is provided a process for

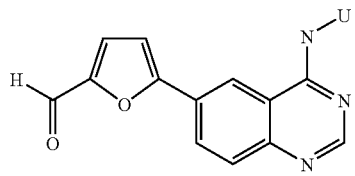

preparing a compound of formula (C), including the steps of:

reacting a compound of formula (A)

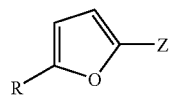

with a compound of formula (B)

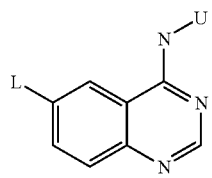

to form the compound of formula (C), wherein U is an organic group; and the compound of formula (A) is generated in situ, and
   L is iodine or bromine;
   R is —C(Q)(T)W where Q and T are independently selected from —OCH$_3$, or
   —OCH$_2$CH$_3$ and W is hydrogen; and
   Z is B(OH)$_2$; or the compound of formula (A) is generated in situ, and
   L is iodine or bromine;
   R is —C(O)H, and
   Z is B(OH)$_2$; or the compound of formula (B) is generated in situ, and
   L is B(OH)$_2$;
   R is —C(O)H; and
   Z is bromine; or the compound of formula (B) is reacted with the compound of formula (A) regioselectively, where neither of the compounds of formula (A) or (B) is generated in situ, and
   L is iodine or bromine;
   R is —C(O)H; and
   Z is hydrogen.

As indicated above U may be any suitable organic group. In one embodiment, U represents a phenyl, pyridyl, 3H-imidazolyl, indolyl, isoindolyl, indolinyl, isoindolinyl, 1H-indazolyl, 2,3-dihydro-1H-indazolyl, 1H-benzimidazolyl, 2,3-dihydro-1H-benzimidazolyl or 1H-benzotriazolyl group, substituted by an R$^2$ group and optionally substituted by at least one independently selected R$^4$ group.

R$^2$ is selected from a group comprising benzyl, halo-, dihalo- and trihalobenzyl, benzoyl, pyridylmethyl, pyridylmethoxy, phenoxy, benzyloxy, halo-, dihalo- and trihalobenzyloxy and benienesulphonyl;

or R$^2$ represents trihalomethylbenzyl or trihalomethylbenzyloxy;

or R$^2$ represents a group of formula

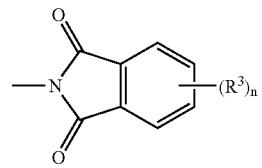

wherein each R$^3$ is independently selected from halogen, C$_{1-4}$alkyl and C$_{1-4}$ alkoxy; and n is 0 to 3.

In a preferred embodiment U represents a phenyl, indolyl, or 1H-indazolyl group substituted by an R$^2$ group and optionally substituted by at least one independently selected R$^4$ group.

In a more preferred embodiment U represents a phenyl or 1H-indazolyl group substituted by an R$^2$ group and optionally substituted by at least one independently selected R$^4$ group.

R$^4$ is selected from the group hydroxy, halo, C$_{1-4}$ alkyl, C$_{2-4}$ alkenyl, C$_{2-4}$ alkynyl, C$_{1-4}$ alkoxy, amino, C$_{1-4}$ alkylamino, di[C$_{1-4}$ alkyl]amino, C$_{1-4}$ alkylthio, C$_{1-4}$ alkylsulphinyl, C$_{1-4}$ alkylsulphonyl, C$_{1-4}$ alkylcarbonyl, carboxy, carbamoyl, C$_{1-4}$ alkoxycarbonyl, C$_{1-4}$ alkanoylamino, N-(C$_{1-4}$ alkyl)carbamoyl, N,N-di(C$_{1-4}$ alkyl)carbamoyl, cyano, nitro and trifluoromethyl.

In a more preferred embodiment, where U represents a phenyl group the group R$^2$ is in the para-position relative to the bond from U to the linking NH group.

In a further more preferred embodiment, where U represents a 1H-indazolyl group the group R$^2$ is in the 1-position of the indazolyl group.

In a preferred embodiment R$^2$ represents benzyl, pyridylmethyl, phenoxy, benzyloxy, halo-, dihalo- and trihalobenzyloxy and benzenesulphonyl.

In a further preferred embodiment R$^2$ represents trihalomethylbenzyloxy.

In a further preferred embodiment R$^2$ represents a group of formula

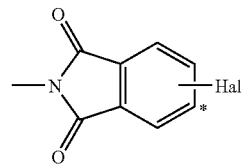

wherein Hal is Br or Cl, particularly Cl, more especially wherein the Hal substituent is in the position marked with a star in the ring as shown.

In a more preferred embodiment R$^2$ represents benzyloxy, fluorobenzyloxy (especially 3-fluorobenzyloxy), benzyl, phenoxy and benzenesulphonyl.

In a further more preferred embodiment $R^2$ represents bromobenzyloxy (especially 3-bromobenzyloxy) and trifluoromethylbenzyloxy.

In a further preferred embodiment, the ring U is not substituted by an $R^4$ group; in an especially preferred embodiment U is phenyl or indazolyl unsubstituted by an $R^4$ group.

In a further preferred embodiment the ring U is substituted by an $R^4$ group selected from halo or $C_{1-4}$ alkoxy; especially chloro, fluoro or methoxy.

In a more preferred embodiment the ring U is substituted by an $R^4$ group wherein $R^4$ represents halo, especially 3-fluoro.

In an especially preferred embodiment U together with $R^4$ represents methoxyphenyl, fluorophenyl, trifluoromethylphenyl or chlorophenyl.

In a more especially preferred embodiment U together with $R^4$ represents methoxyphenyl or fluorophenyl.

In an especially preferred embodiment the group U together with the substituent(s) $R^2$ and $R^4$ represents benzyloxyphenyl, (fluorobenzyloxy)phenyl, (benzenesulphonyl)phenyl, benzylindazolyl or phenoxyphenyl.

In a more especially preferred embodiment the group U together with the substituent(s) $R^2$ and $R^4$ represents benzyloxyphenyl, (3-fluorobenzyloxy)phenyl, (benzenesulphonyl)phenyl or benzylindazolyl.

In another more especially preferred embodiment the group U together with the substituent(s) $R^2$ and $R^4$ represents (3-bromobenzyloxy)phenyl, (3-trifluoromethylbenzyloxy)phenyl, or (3-fluorobenzyloxy)-3-methoxyphenyl.

In another more especially preferred embodiment the group U together with the substituent(s) $R^2$ and $R^4$ represents 3-fluorobenzyloxy-3-chlorophenyl, benzyloxy-3-chlorophenyl, benzyloxy-3-trifluoromethylphenyl, (benzyloxy)-3-fluorophenyl, (3-fluorobenzyloxy)-3-fluorophenyl or (3-fluorobenzyl)indazolyl.

In a most especially preferred embodiment the group U together with the substituent(s) $R^2$ and $R^4$ represents benzyloxyphenyl or (3-fluorobenzyloxy)phenyl.

Halo is, for example, fluoro, chloro, bromo or iodo; preferably it is fluoro, chloro or bromo, more preferably fluoro or chloro.

$C_{1-4}$ alkyl is, for example, methyl, ethyl, propyl, isopropyl, butyl, isobutyl, sec-butyl or tert-butyl; preferably it is methyl, ethyl, propyl, isopropyl or butyl, more preferably methyl.

$C_{2-4}$ alkenyl is, for example, ethenyl, prop-1-enyl or prop-2-enyl; preferably it is ethenyl.

$C_{2-4}$ alkynyl is, for example, ethynyl, prop-1-ynyl or prop-2-ynyl; preferably it is ethynyl.

$C_{1-4}$ alkoxy is, for example, methoxy, ethoxy, n-propoxy, isopropoxy, n-butoxy, isobutoxy, sec-butoxy or tert-butoxy; preferably it is methoxy, ethoxy, propoxy, isopropoxy or butoxy; more preferably it is methoxy.

$C_{1-4}$ alkylamino is, for example, methylamino, ethylamino or propylamino; preferably it is methylamino.

di[$C_{1-4}$ alkyl]amino is, for example, dimethylamino, diethylamino, N-methyl-N-ethylamino or dipropylamino; preferably it is dimethylamino.

$C_{1-4}$ alkylthio is, for example, methylthio, ethylthio, propylthio or isopropylthio, preferably methylthio.

$C_{1-4}$ alkylsulphinyl is, for example, methylsulphinyl, ethylsulphinyl, propylsulphinyl or isopropylsulphinyl, preferably methylsulphinyl.

$C_{1-4}$ alkylsulphonyl is, for example, methanesulphonyl, ethylsulphonyl, propylsulphonyl or isopropylsulphonyl, preferably methanesulphonyl.

$C_{1-4}$ alkylcarbonyl is, for example methylcarbonyl, ethylcarbonyl or propylcarbonyl.

$C_{1-4}$ alkoxycarbonyl is, for example, methoxycarbonyl, ethoxycarbonyl, propoxycarbonyl, butoxycarbonyl or tert-butoxycarbonyl.

$C_{1-4}$ alkanoylamino (where the number of carbon atoms includes the CO functionality) is, for example, formamido, acetamido, propionamido or butyramido.

N—($C_{1-4}$ alkyl)carbamoyl is, for example, N-methylcarbamoyl or N-ethylcarbamoyl.

N,N-di($C_{1-4}$ alkyl)carbamoyl is, for example, N,N-dimethylcarbamoyl, N-methyl-N-ethylcarbamoyl or N,N-diethylcarbamoyl.

The following examples are intended for illustration only and are not intended to limit the scope of the invention in any way. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| N (Normal) | Kg (kilogram) |
| i. v. (intravenous); | Hz (Hertz); |
| MHz (megahertz); | mol (moles); |
| mmol (millimoles); | RT (room temperature); |
| min (minutes); | h (hours); |
| mp (melting point); | TLC (thin layer chromatography); |
| $T_r$ (retention time); | RP (reverse phase); |
| THF (tetrahydrofuran); | DMSO (dimethylsulfoxide); |
| EtOAc (ethyl acetate); | DME (1,2-dimethoxyethane); |
| DCM (dichloromethane); | DCE (dichloroethane); |
| DMF (N,N-dimethylformamide); | HOAc (acetic acid); |
| TMSE (2-(trimethylsilyl)ethyl); | TMS (trimethylsilyl); |
| TIPS (triisopropylsilyl); | TBS (t-butyldimethylsilyl); |
| HPLC (high pressure liquid chromatography); | |

Unless otherwise indicated, all temperatures are expressed in ° C. (degrees Centigrade). All reactions conducted under an inert atmosphere at room temperature unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet, br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 50/% ethanolic phosphomolybdic acid or p-anisaldehyde solution. Flash column chromatography was performed on silica gel (230–400 mesh, Merck). Optical rotations were obtained using a Perkin Elmer Model 241 Polarimeter. Melting points were determined using a Mel-Temp II apparatus and are uncorrected.

Example 1

Preparation of 5-(4-[3-chloro-4-(3-fluorobenzyloxy)-anilino]-6-quinazolinyl)-furan-2-carbaldehyde To a reaction vessel was added N-{3-chloro-4-[(3-fluorobenzyl)oxy]phenyl}-6-iodo-4-quinazolinamine (100 mg; 0.198 mmol), 2-formylfuran-5-boronic acid (Frontier Scientific, 42 mg; 0.297 mmol), 10% palladium on activated carbon (5 mg; 0.05 wt), DME (2.0 mL), MeOH (1.0 mL) and triethylamine (83 µL). After heating at 50° C. for 14 h, a HPLC indicated 98.5% clean conversion. $^1$H NMR (d$_6$-DMSO) δ: 11.44 (s, 1H), 9.38 (s, 2H), 9.11 (s, 1H), 8.90 (s, 1H), 8.39 (dd, 1H, J=8 and 4 Hz), 7.89 (d, 1H, J=12 Hz), 7.84 (d, 1H, J=4 Hz), 7.60 (dd, 1H, J=8 and 4 Hz), 7.47–7.42 (m, 2H), 7.44 (AA'BB', 2H, $J_{AB}$=8 Hz), 7.35–7.25 (m, 3H), 7.24 (d, 1H, J=4 Hz), 7.16 (dt, 1H, J=8 and 4 Hz), 7.06 (AA'BB', 2H, $J_{AB=}$8 Hz, 6.84 (d, 1H, J=4 Hz), 5.27 (s, 2H), 4.43 (s, 2H), 3.61–3.50 (m, 2H), 3.47–3.36 (m, 2H), 3.09 (s, 3H), 2.23 (s, 6H).

Example 2

Preparation of 5-(4-[3-chloro-4-(3-fluorobenzyloxy)-anilino]-6-quinazolinyl)-furan-2-carbaldehyde (i) In situ Preparation of 2-diethylacetal-furan-5-boronica acid A 20 L reaction vessel was charged with 6.7 volumes of DME and 0.67 wt., (740 grams, 410 mL, 4.35 mol) of 2-furaldehyde diethyl acetal and cooled to −40° C. under reaction/contents control. n-Butyllithium, 1.32 wt. (2.5 M in hexanes, 1.45 kg, 5.22 mole) was added over ca. 40 minutes using a ChemTech CP120 metering pump containing a ceramic head. The internal temperature rose to −31° C. The reaction mixture turned very dark, but was homogeneous. After the addition was complete, the lines were flushed with ca. 0.17 volumes of hexane directly into the reaction vessel. When the internal temperature decreased to −40° C., the reaction mixture was stirred for an additional 2.5 hrs. After 2.5 hours, 1.1 vol (0.89 wt, 982 grams, 5.22 mol) of triisopropylborate was added via the metering pump over 20 minutes. A slight exotherm was observed during the first half of the addition, which peaked at about −31° C. An additional 0.15 vol of hexane was used to flush the pump lines into the reaction tank. After 2 hours, (with 30 minutes at −40° C.), the temperature of the reaction was ramped up to 25° C. over 60 minutes. When the internal temperature reached 25° C., a 1 mL aliquot was removed for an in-process check. [Sample preparation: Two drops of the reaction mixture were diluted with 1 mL of CH$_3$CN and 100 µL of 1N HCl and subjected to LC at 280 nM.] The boronic acid/2-furfural ratio was 119:1. At this point, 0.29 vol of acetic acid was added and the reaction mixture was stirred for 30 minutes. Water, 0.36 vol, was added after 30 min. This reaction mixture was used directly in the next step.

(ii) Preparation of 5-(4-[3-chloro-4-(3-fluorobenzyloxy)-anilino]-6-quinazolinyl)-furan-2-carbaldehyde 4-methyl-benzenesulfonate Using in situ Prepared 2-diethylacetal-5-boronic acid To the reaction mixture from above was added 3.4 vol (3.7 L) of ethanol over a 5 minute period via vacuum addition. Triethylamine, 0.69 vol (760 mL, 5.45 mol) was added followed by 1 wt (1100 g, 2.18 mol) of N-{3-chloro-4-[(3-fluorobenzyl)oxy]phenyl}-6-iodo-4-quinazolinamine and 3 wt % of 10% Pd/C [Palladium, 10 wt % (dry basis) on Activated Carbon, 50% Water Wet, Degussa Type E101NE/W]. The reactor, in reactor control mode, was set to 62° C. The internal temperature was observed to rise to 58° C. over ca. 2 hrs. After ca. 14 hours, an aliquot was removed for an in-process check. [Sample preparation: 15 µL was diluted with 1 mL of MeOH and 250 µL of 1 N HCl and subjected to Fast LC at 220 nM.] At this time, the reactor was cooled to 25° C. The dark reaction mixture was transferred to the second reactor through a teflon-lined stainless steel jacketed transfer hose outfitted with an in-line 5.0 µm cartridge filter (Pall part no. R1f050, lot no. FJ0807) and an in-line 0.45 µm filter (Meisner CLMF 0.4–662, lot no. 4087-R-#F). The first reactor was rinsed with 0.5 vol of DME and was passed through the transfer hose so as to wash the solids through the filter cartridges. p-Toluenesulfonic acid monohydrate, 1.55 wt (1700 g, 8.72 mol) was dissolved in 2.27 vol of deionized water and the solution was added to the reaction mixture over 5 minutes. After stirring at 25° C. for 1 hour, the product was collected in a ceramic filter lined with medium filter paper. The reactor and filter cake were rinsed with 0.9 vol of a 1:1 DME/water solution. After suctioning dry for 4 hours, the yellow filter cake was transferred to two glass trays and placed in the drying oven (50–55° C.) under house vacuum (18 in Hg) with a nitrogen bleed. The two glass trays were removed from the oven and allowed to cool to room temperature and sampled accordingly. The isolated yield of the title compound was 1230 grams (1.12 wt., 87% th; 1410 g Th) which existed as a yellowish solid. $^1$H NMR (d$_6$-DMSO) δ: 11.44 (s, 1H), 9.38 (s, 2H), 9.11 (s, 1H), 8.90 (s, 1H), 8.39 (dd, 1H, J=8 and 4 Hz), 7.89 (d, 1H, J=12 Hz), 7.84 (d, 1H, J=4 Hz), 7.60 (dd, 1H, J=8 and 4 Hz), 7.47–7.42 (m, 2H), 7.44 (M'BB', 2H, $J_{AB}$=8 Hz), 7.35–7.25 (m, 3H), 7.24 (d, 1H, J=4 Hz), 7.16 (dt, 1H, J=8 and 4 Hz), 7.06 (AA'BB', 2H, $J_{AB}$=8 Hz, 6.84 (d, 1H, J=4 Hz), 5.27 (s, 2H), 4.43 (s, 2H), 3.61–3.50 (m, 2H), 3.47–3.36 (m, 2H), 3.09 (s, 3H), 2.23 (s, 6H).

Example 3

Preparation of 5-(4-[3-chloro-4-(3-fluorobenzyloxy)-anilino]-6-quinazolinyl)-furan-2-carbaldehyde Using in situ Protected 2-furaldehyde N,O-dimethylhydroxylamine hydrochloride (629 mg; 6.32 mmol) was suspended in THF (19 mL; 40 Vol), and the flask was cooled to −40° C. (Cryocool-controlled isopropanol bath). n-Butyllithium (2.5 M solution in hexanes; 5.3 mL; 13.2 mmol) was added at a dropwise rate while the internal temperature rose to −12° C. However, the mixture quickly cooled back to −40° C. After 30 min at −40° C., 2-furaldehyde (481 µL; 5.74 mmol) was rapidly added to the mixture which caused the internal temperature to rise to −28° C. Again, the temperature dropped quickly back to −40° C. After 15 min at −40° C., n-butyllithium (2.5 M solution in hexanes; 2.8 mL; 6.89 mmol) was added at a dropwise rate, while the internal temperature was maintained below −35° C. During the course of addition, the mixture turned yellow. After the addition was complete, the mixture was allowed to stir at −40° C. for 1 h. Triisopropylborate (2.0 mL; 8.62 mmol) was added at a dropwise rate, while the internal temperature was maintained below −35° C. After the addition was complete, the cooling was turned off. A HPLC indicated 83.7% of desired boronic acid, 6.2% of starting material. When the internal temperature reached −20° C., the mixture was quenched by addition of acetic acid (462 μL; 8.04 mmol) and allowed to warm to ambient temperature. The material was advanced without purification or isolation directly to the Suzuki Coupling reaction.

To the reaction vessel containing crude boronic acid was added N,N-dimethylacetamide (13 mL), 1.16 M aqueous $Na_2CO_3$ solution (7.3 mL; 7.38 mmol), N-{3-chloro-4-[(3-fluorobenzyl)oxy]phenyl}-6-iodo-4-quinazolinamine (1.87 g; 3.69 mmol), and dichloro[1,1'-bis(diphenylphosphino)ferrocene]palladium(II) dichloromethane adduct (15 mg; 0.0185 mmol). Upon addition of the base, the internal temperature rose to ca. 28° C. The reaction mixture was heated to 50° C. (internal temperature) with an oil bath. The reaction mixture was filtered through a compressed pad of Celite and the solids were washed with THF. The isolated solution was then diluted with ethyl acetate and aqueous hydrochloric acid was added. The layers were separated and the aqueous was neutralized and diluted with ethyl acetate. The layers were separated and the organic layer was dried over sodium sulfate, filtered and concentrated under vacuum to give the title compound. LC retention time of title compound: 4.9 minutes.

Example 4

Preparation of 5-(4-[3-chloro-4-(3-fluorobenzyloxy)-anilino]-6-quinazolinyl)-furan-2-carbaldehyde Hydrochloride Using in situ Protected 5-bromo-2-furaldehyde N,O-dimethylhydroxylamine hydrochloride (3.04 g; 30.49 mmol) was suspended in THF (40 mL), and the flask was cooled to −78° C. (dry ice—acetone bath). n-Butyllithium (2.5 M solution in hexanes; 24.4 mL; 60.98 mmol) was added dropwise to this cold suspension, which became homogeneous. The acetone/$CO_2$ bath was replaced by a water/ice bath (0° C.), and the mixture turned pale yellow. After stirring for 15 min at 0° C., the solution was cooled back to −78° C., and 5-bromo-2-furaldehyde (5.00 g dissolved in 10 mL of THF; 27.72 mmol) was added at a dropwise rate. Fifteen minutes after the addition had been completed, the reaction mixture was allowed to warm to 0° C. in a water/ice bath, and 15 minutes later, it was cooled back to −78° C. ten minutes later, triisopropylborate (18.8 mL; 83.16 mmol) was added to the cold mixture in one portion, followed by dropwise addition of n-butyllithium (2.5 M solution in hexanes; 27.7 mL; 69.30 mmol). After 30 min at −78° C., acetic acid (6.5 mL; 102.6 mmol) was added to the cold reaction mixture, which was then allowed to warm to ambient temperature. The material was advanced without purification or isolation directly to the Suzuki Coupling reaction.

To the reaction vessel containing crude boronic acid was added N,N-dimethylacetamide (54 mL), water (11 mL), N-{3-chloro-4-[(3-fluorobenzyl)oxy]phenyl}-6-iodo-4-quinazolinamine (10.78 g; 21.32 mmol), solid $Na_2CO_3$ (6.85 g; 63.97 mmol), and dichloro[1,1'-bis(diphenylphosphino)ferrocene]palladium(II) dichloromethane adduct (174 mg; 0.21 mmol) to yield an orange reaction mixture. The reaction mixture was heated to 80° C., and no color change was noted. After 28.5 h total reaction time, the reaction mixture was allowed to cool to ambient temperature. The mixture was diluted with THF (54 mL), treated with 100 mesh Darco® G-60 Activated Carbon (696 mg), Hyflo Super Cel® (348 mg) and stirred at ambient temperature for >2 h. The precipitates were removed by suction filtration through fritted funnel loaded with Hyflo Super Cel® and washed with THF (5×22 mL) until the THF solvent displayed no more color. The filtrate was treated with concentrated aqueous HCl (7.1 mL; 85.3 mmol) and water (80 mL) and allowed to stir at ambient temperature for 2 h. The precipitate was filtered through a fritted funnel and rinsed with 33% isopropanol/water (54 mL), water (54 mL) and 33% isopropanol/water (54 mL), and then allowed to air-dry for 2 h. The yellowish brown solid was transferred into a vacuum desiccator and allowed to dry in vacuo overnight. The reaction gave 9.01 g of the title compound (83% yield) as a beige-brown powder. LC retention time of title compound: 4.9 minutes.

Example 5

Preparation of 5-(4-[3-chloro-4-(3-fluorobenzyloxy)-anilino]-6-quinazolinyl)-furan-2-carbaldehyde Using in situ Generated 4-{3-chloro-4-[(3-fluorobenzyl]oxylanilino}-6-quinazolinylboronie acid N-{3-Chloro-4-[(3-fluorobenzyl)oxy]phenyl}-6-iodo-4-quinazolinamine (200 mg; 0.395 mmol) was dissolved in THF (2.0 mL), giving a yellowish solution. The mixture was cooled to 0° C. (water/ice bath) and then treated with ethylmagnesium bromide (1.0 M solution in THF; 475 μL; 0.475 mmol) to yield a homogeneous bright yellow solution, which was cooled, to −78° C. Triisopropylborate (373 μL; 1.582 mmol) was added rapidly, followed by slow addition of n-butyllithium (2.5 M solution in hexanes; 395 μL; 0.989 mmol). When the reaction completed as verified by HPLC, acetic acid (84 μL; 1.463 mmol) was added to quench the reaction. To the crude yellow slurry of boronic acid in THF was added 5-bromo-2-furaldehyde (107 mg; 0.593 mmol), followed by N,N-dimethylacetamide (2.0 mL), which caused the mixture to become homogeneous, 1.016 N aqueous $Na_2CO_3$ (1.2 mL; 1.185 mmol) and finally dichloro[1,1'-bis(diphenylphosphino)ferrocene]palladium(II) dichloromethane adduct (16 mg; 0.020 mmol). The mixture was heated at 80° C. A HPLC check after 15 h indicated 95% clean conversion to the title compound. LC retention time: t=4.9 min.

Example 6

Regioselective Preparation of 5-(4-[3-chloro-4-(3-fluorobenzyloxy)-anilino]-6-quinazolinyl)-furan-2-carbaldehyde 4-methylbenzenesulfonate A mixture of 2-furaldehyde (5.7 mL, 69 mmol), potassium acetate (1.4 g, 14 mmol), and palladium(II)chloride (61 mg, 0.35 mmol) in 35 mL of DMF was degassed for 10 minutes by vigorously bubbling $N_2$ through the mixture while stirring. The catalyst mixture was subsequently warmed to 110° C. A solution of N-{3-chloro-4-[(3-fluorobenzyl)oxy]phenyl}-6-iodo-4-quinazolinamine (3.5 g, 6.9 mmol) in 55 mL of DMF was degassed in a similar manner and then added to the catalyst mixture via syringe pump over 10 hours. After the addition was complete, the reaction temperature was maintained at 110° C. for an additional two hours. After cooling to room temperature, the mixture was poured into 125 mL of water. The precipitate was collected on coarse filter paper and washed with water (ca. 7 mL). The solid was re-dissolved in warm (50° C.) DME. To this solution was added (2.0 g; 10.4 mmol) of p-toluenesuflonic acid monohydrate. The temperature was lowered to 35° C. and the mixture was stirred at this temperature overnight Water (60 mL) was added to induce further precipitation. The product was collected on coarse filter paper and subsequently washed with 30–40 mL of DME/water (1:1). The filter cake was dried at 50° C. under house vacuum overnight to provide 2.5 g (55%) of the title compound. $^1$H NMR ($d_6$-DMSO) δ: 11.44 (s, 1H), 9.38 (s, 2H), 9.11 (s, 1H), 8.90 (s, 1H), 8.39 (dd, 1H, J=8 and 4 Hz), 7.89 (d, 1H, J=12 Hz), 7.84 (d, 1H, J=4 Hz), 7.60 (dd, 1H, J=8 and 4 Hz), 7.47–7.42 (m, 2H), 7.44 (AA'BB', 2H, $J_{AB}$=8 Hz), 7.35–7.25 (m, 3H), 7.24 (d, 1H. J=4 Hz), 7.16 (dt, 1H, J=8 and 4 Hz), 7.06 (AA'BB', 2H, $J_{AB}$=8 Hz, 6.84 (d, 1H, J=4 Hz), 5.27 (s, 2H), 4.43 (s, 2H), 3.61–3.50 (m, 2H), 3.47–3.36 (m, 2H), 3.09 (s, 3H), 2.23 (s, 6H).

Example 7

Preparation of 5-(4-[3-chloro-4-(3-fluorobenzyloxy)-anilino]-6-quinazolinyl)-furan-2-carbaldehyde 4-methylbenzenesulfonate A 2 liter, 3 neck round bottom flask equipped with a mechanical stirrer was charged with 74.95 grams of the HCl salt of 5-(4-[3-chloro-4-(3-fluorobenzyloxy)-anilino]-6-quinazolinyl)-furan-2-carbaldehyde (prepared according to Procedure C, page 56 of WO 99/35146: See Scheme A, Procedure C above) and 749.5 mL THF. To this slurry was charged 84.45 mL of 2M NaOH and the reactants were stirred for 30 minutes. The layers were separated and then the organic layer was washed with 160 mL of $H_2O$. The organic layer was slurried with 3.75 grams of Darco G60 and filtered through celite. The filtrate was collected and slowly added to 33.54 grams of toluenesulfonic acid monohydrate with rapid stirring. The solids slowly precipitated out at ambient temperature. The mixture was cooled to 0° C. and stirred for 10 min. The mixture was filtered and pulled dry with a rubber dam, then dried in vacuo at 50° C. overnight. The yield of 5-(4-[3-chloro-4-(3-fluorobenzyloxy)-anilino]-6-quinazolinyl)-furan-2-carbaldehyde 4-methylbenzene sulfonate was 84.25 grams (88.8%).

Example 8

Preparation of N-{3-Chloro-4-[(3-fluorobenzyl) oxy]phenyl}-6-[5-({[2-(methanesulphonyl)ethyl]amino}methyl)-2-furyl]-4-quinazolinamine ditosylate anhydrate (Anhydrate Form of Compound of Formula II)

To a 20 L reactor was added 13.3 vol of THF followed by 0.62 wt (2.93 mol) of NaBH(OAc)$_3$. The 20 L reactor was set to maintain contents at 20° C. A second 20 L reactor was charged with 1000 grams, (1.55 mol) of 5-(4-[3-chloro-4-(3-fluorobenzyloxy)-anilino]-6-quinazolinyl)-furan-2-carbaldehyde 4-methyl benzenesulfonate prepared by the procedure of Example 7 and 6.7 vol of THF. To the THF solution of 5-(4-[3-chloro-4-(3-fluorobenzyloxy)-anilino]-6-quinazolinyl)-furan-2-carbaldehyde 4-methylbenzenesulfonate was added 0.325 vol (1.86 mol) diisopropylethylamine followed by 0.32 wt of 2-(methylsulfone)ethylamine, (321 g, 2.6 mol) and 0.15 vol of IPA. After 1 hour, the preformed imine/THF solution was transferred by vacuum to the stirred suspension of NaBH(OAc)$_3$ in the first 20 L reactor over 10 minutes. After 90 minutes, 4 vol of 5N NaOH was added over 40 min via a pump. This solution was allowed to stir for 15 minutes after which the stirrer was switched off and the layers were allowed to separate. The aqueous layer was drained from the bottom of the reactor and the organic layer transferred to the empty 20 L reactor through a teflon-lined stainless steel jacketed transfer hose outfitted with an in-line 0.45 μm filter. To this solution was added a 2 vol THF solution of 4 wt (1180 g, 6.2 mole) of p-toluenesulfonic acid monohydrate over 5 min. A yellowish precipitate was observed to come out of solution and this was allowed to stir at room temperature for 12 hours. The reaction was drained from the bottom of the reactor and filtered through a ceramic filter lined with paper. The yellow filter cake was washed with 1 vol of a 95:5 THF/water solution and allowed to air dry overnight. After suctioning dry for 12 hours, the yellow filter cake was transferred to two glass trays and placed in the drying oven (42° C.) under house vacuum (18 in Hg) with a nitrogen bleed. The two glass trays were removed from the oven and allowed to cool to room temperature and sampled accordingly. The isolated yield of N-{3-Chloro-4-[(3-fluorobenzyl) oxy]phenyl}-6-[5-({[2-(methane-sulphonyl)ethyl]amino}methyl)-2-furyl]-4-quinazolinamine ditosylate (anhydrate) was 1264 grams (1.3 wt, 88%; 1443 g Th) and was a yellow solid.

Approximately 50 mg of the product was transferred to a Karl Fisher Volumetric Moisture Apparatus (model DL35, Mettler, Hightstown, N.J.), which was operated according to the manufacturer's instructions. The anhydrate water content was determined to be 0.31%.

Example 9

X-Ray Diffraction of Anhydrate Ditosylate Salt

An anhydrate ditosylate salt sample prepared according to Example 8 was dusted on to a silicon zero background plate of a Scintag XDS2000 Diffractometer. The powder x-ray diffraction pattern of the sample was obtained under the following conditions.

| | |
|---|---|
| Geometry: | θ/θ |
| Asset: | 0038018 |
| Seifert High Voltage ID3000 generator, S/N 90 67 1422 | |
| X-ray tube tower: Seifert type V4, 60 kV max, 40 mA max, | |
| X-ray diffraction tube: AEG FK-60-10 copper anode tube, | |
| 60 kV max, 2 kW max, | |
| normal focus (1 × 10 mm) | |
| Scintag Peltier cooled Si(Li) Solid State Detector Model B3A, | |
| Goniometer radius: | 250 mm |
| Operating Conditions: | |
| X-ray tube voltage: | 45 kV |
| X-ray tube current: | 40 mA |
| Scan Conditions: | |
| chopper: | 0.02 deg |
| continuous scan mode | |
| scan rate: | 0.1 deg 2θ/min |
| sample spinner: | ON (1 rotation/sec) |
| DS = 1 mm; SS(i) = 2 mm | |
| SS(d) = 0.5 mm; HS = 0.3 mm | |
| DS = divergent slit (incident beam) | |
| SS(i) = scatter slit (incident) | |
| SS(d) = scatter slit (diffracted) | |
| RS = receiving slit | |

The data was obtained and analyzed using DMSNT v. 1.37 software available from Scintag, Inc. The x-ray diffraction pattern obtained is shown in FIG. 1.

Example 10

Preparation of N-{3-Chloro-4-[(3-fluorobenzyl) oxy]phenyl}-6-[5-({[2-(methanesulphonyl)ethyl] amino}methyl)-2-furyl]-4-quinazolinamine ditosylate monohydrate (Monohydrate Form of Compound of Formula II)

A 20 L reactor was charged with 1 wt (930 g, 1.0 mol) of N-{3-Chloro-4-[(3-fluorobenzyl) oxy]phenyl}-6-[5-({[2-(methanesulphonyl)ethyl]amino}methyl)-2-furyl]-4-quinazolinamine ditosylate anhydrate prepared using the procedure of Example 8. To this was added 10 volumes of a pre-mixed 8:2 THF:deionized water solution and the reactor was heated to 65° C. Complete dissolution was observed at 50° C. The clear reaction mixture was transferred to another 20 L reactor through a stainless steel jacketed transfer hose that was equipped with an in-line 5.0 μm cartridge filter. The empty 20 L reactor and the filter line were washed with 0.2 vol of the pre-mixed 8:2 THF: deionized water solution. An additional 1 vol of pre-mixed 8:2 THF:deionized water solution was used to wash the material into the reaction mixture. The 20 L reactor was heated to ~80° C. The reaction temperature was then ramped down to 55° C. over 2 hours and then to 45° C. over 10 hours. After 10 hours, the temperature was adjusted to 25° C. and the reaction mixture allowed to stir at room temperature for 45 minutes. The yellow precipitate was drained from the bottom of the 20 L reactor into a ceramic filter lined with paper. The flow was fast and smooth and the filter rate very good. The yellow filter cake was washed with 0.6 volumes of a pre-mixed 8:2 THF:deionized water solution and the yellow solid was air dried for 4 hours and placed into a glass tray. The glass tray was placed in a vacuum oven under house vacuum (~18 in Hg) at 60° C. with a nitrogen bleed for 2 days. After removal from the oven, the material was sampled accordingly. The yield was 743 grams (0.8 wt, 80%; 930 g th) as a bright yellow, crystalline solid.

Approximately 50 mg of the product was transferred to a Karl Fisher Volumetric Moisture Apparatus (model DL35, Mettler, Hightstown, N.J.), which was operated according to the manufacturer's instructions. The monohydrate water content was determined to be 1.99%, which is in agreement with the theoretical value of 1.92%.

Example 11

X-Ray Diffraction of Monohydrate Ditosylate Salt

A monohydrate ditosylate salt sample prepared according to Example 10 was dusted on to a silicon zero background plate of a Scintag XDS2000 Diffractometer. The powder x-ray diffraction pattern of the sample was obtained under the following conditions.

| | |
|---|---|
| Geometry: | θ/θ |
| Asset: | 0038018 |
| Seifert High Voltage ID3000 generator, S/N 90 67 1422 | |
| X-ray tube tower: Seifert type V4, 60 kV max, 40 mA max, | |
| X-ray diffraction tube: AEG FK-60-10 copper anode tube, 60 kV max, 2 kW max, | |
| normal focus (1 × 10 mm) | |
| Scintag Peltier cooled Si(Li) Solid State Detector Model B3A | |
| Goniometer radius: | 250 mm |
| Operating Conditions: | |
| X-ray tube voltage: | 45 kV |
| X-ray tube current: | 40 mA |
| Scan Conditions: | |
| chopper: continuous scan mode | 0.02 deg |
| scan rate: | 0.25 deg 2θ/min |
| sample spinner: | ON (1 rotation/sec) |
| DS = 1 mm; SS(i) = 2 mm | |
| SS(d) = 0.5 mm; RS = 0.3 mm | |
| DS = divergent slit (incident beam) | |
| SS(i) = scatter slit (incident) | |
| SS(d) = scatter slit (diffracted) | |
| RS = receiving slit | |

Figure 2:
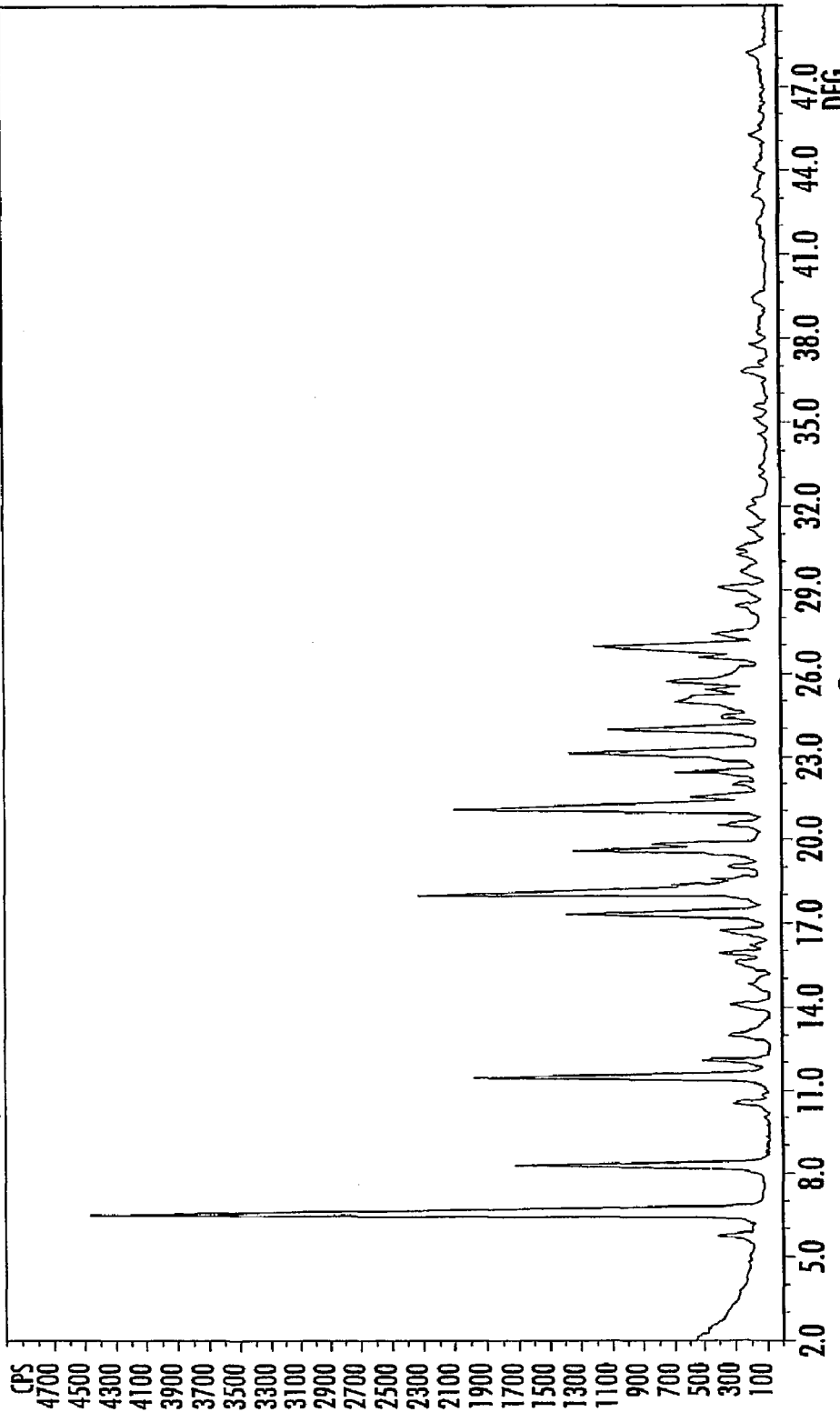
FIG. 2 depicts the powder X-ray diffraction pattern of N-{3-Chloro-4-[(3-fluorobenzyl) oxy]phenyl}-6-[5-({[2-(methanesulphonyl)ethyl] amino}methyl)-2-furyl]-4-quinazolinamine ditosylate monohydrate.

The data was obtained and analyzed using DMSNT v. 1.37 software available from Scintag, Inc., The x-ray diffraction pattern obtained is shown in FIG. 2.

Example 12

Preparation of (4-(3-Fluoro-benzyloxy)-3-bromophenyl)-(6-(5-((2-methanesulphonyl-ethylamino)-methyl)-furan-2-yl)quinazolin-4-yl)-amine Ditosylate. (Compound of Formula IV)

The HCl salt of 5-(4-[3-bromo-4-(3-fluorobenzyloxy)-anilino]-6-quinazolinyl)-furan-2-carbaldehyde (prepared according to Procedure C, page 56 of WO 99/35146) was converted to the tosylate salt according to the procedure of Example 7. The resultant furan 2-carbaldehyde tosylate product was used to prepare the (4-(3-Fluoro-benzyloxy)-3-bromophenyl)-(6-(5-((2-methanesulphonyl-ethylamino)-methyl)-furan-2-yl)quinazolin-4-yl)-amine ditosylate according to the procedure of Example 8.

Example 13

Preparation of (4-(3-Fluoro-benzyloxy)-3-chlorophenyl)-(6-(2-((2-methanesulphonyl-ethylamino)-methyl)-thiazol-4-yl)quinazolin-4-yl)-amine ditosylate (Compound of Formula III)

The HCl salt of (4-(3-Fluoro-benzyloxy)-3-chlorophenyl)-(6-(2-((2-methanesulphonyl-ethylamino)-methyl)-thiazol-4-yl)quinazolin-4-yl)-amine was prepared according to Procedure F, pages 57–59 of WO 99/35146 and then converted to the (4-(3-Fluoro-benzyloxy)-3-chlorophenyl)-(6-(2-((2-methanesulphonyl-ethylamino)-methyl)-thiazol-4-yl) quinazolin-4-yl)-amine ditosylate salt according to the procedures of Example 7.

Example 14

Conversion of N-{3-Chloro-4-[(3-fluorobenzyl) oxy]phenyl}-6-[5-({[2-(methanesulphonyl)ethyl] amino}methyl)-2-furyl]-4-quinazolinamine ditosylate-monohydrate to anhydrate Approximately 50 mg of N-{3-Chloro-4-[(3-fluorobenzyl) oxy]phenyl}-6-[5-({[2-(methanesulphonyl)ethyl] amino}methyl)-2-furyl]-4-quinazolinamine ditosylate monohydrate prepared according to the procedure of Example 10 was weighed into a 1-dram vial to which 1-mL of MeOH or 2-methoxyethanol was added. The slurry was stirred in a 25° C. water bath for 4 days, after which the solid was separated by filtration and dried under house vacuum at 40° C. for 1 day. The x-ray diffraction pattern of the dried solid from both MeOH and 2-methoxyethanol matched that of N-{3-Chloro-4-[(3-fluorobenzyl) oxy]phenyl}-6-[5-({[2-(methanesulphonyl)ethyl]amino}methyl)-2-furyl]-4-quinazolinamine ditosylate anhydrate.

Example 15

Conversion of N-{3-Chloro-4-[(3-fluorobenzyl) oxy]phenyl}-6-[5-({[2-(methanesulphonyl)ethyl] amino}methyl)-2-furyl]-4-quinazolinamine ditosylate- anhydrate to monohydrate To a 1 L 3-necked round bottomed flask equipped with an overhead stirrer was placed 77.0 g (0.08 mol) N-(3-Chloro-4-[(3-fluorobenzyl) oxy]phenyl}-6-[5-({[2-(methanesulphonyl)ethyl]amino}methyl)-2-furyl]-4-quinazolinamine ditosylate anhydrate prepared according to the procedure of Example 12. To the yellow solid was added deionized water (10 vols) and the slurry was left to stir at RT. At one hour time points, small aliquots were removed, filtered through paper on a Buchner funnel and dried in a vacuum oven at 60° C. for 12 hrs. Each sample was submitted for XRD analysis [t=45 min, anhydrate; t=2.5 hrs, anhydrate; t=3.5 hrs, mixture of anhydrate/monohydrate; t=>12 hrs, monohydrate.] The reaction slurry was left to stand at room temperature for 36 hrs. The bright yellow material was then filtered through paper on a Buchner funnel and air dried overnight. The material was placed in a vacuum drying oven at 55° C. with a nitrogen bleed for 96 hrs. The isolated yield was 74 grams (96% Th). A sample was submitted for XRD which indicated it was N-{3-Chloro-4-[(3-fluorobenzyl) oxy]phenyl}-6-[5-({[2-(methanesulphonyl)ethyl]amino}methyl)-2-furyl]-4-quinazolinamine ditosylate monohydrate.

Example 16

Figure 3A:
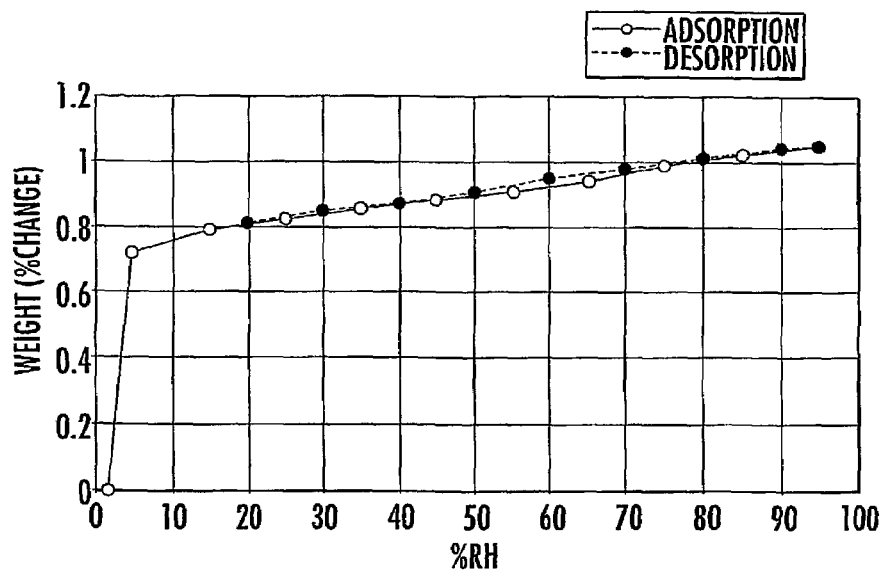
FIGS. 3(a) and (b) depict water sorption curves of (a) N-{3-Chloro-4-[(3-fluorobenzyl) oxy]phenyl}-6-[5-({[2-(methanesulphonyl)ethyl]amino}methyl)-2-furyl]-4-quinazolinamine monohydrate ditosylate and (b) N-{3-Chloro-4-[(3-fluorobenzyl) oxy]phenyl}-6-[5-({[2-(methanesulphonyl)ethyl]amino}methyl)-2-furyl]-4-quinazolinamine di-HCl salt.

Moisture Sorption Testing N-{3-Chloro-4-[(3-fluorobenzyl) oxy]phenyl}-6-[5-({[2-(methanesulphonyl)ethyl]amino}methyl)-2-furyl]-4-quinazolinamine ditosylate monohydrate salt Approximately 12 mg of N-{3-Chloro-4-[(3-fluorobenzyl) oxy]phenyl}-6-[5-({[2-(methanesulphonyl)ethyl] amino}methyl)-2-furyl]-4-quinazolinamine ditosylate monohydrate salt prepared according to Example 10 was weighed into a sample pan of a moisture sorption apparatus (model number SGA-100, made by VTI). The sample was dried at 60° C. under a nitrogen stream until the weight loss was less than 0.015% in 5 minutes. The relative humidity (RH) was then increased (adsorption) to 5, 15, 25, 35, 45, 55, 65, 75, 85 and 95%—at each step, equilibrium was defined as a weight change of less than 0.015% in 5 minutes. The relative humidity was then decreased (desorption) to 90, 80, 70, 60, 50, 40, 30, and 20% with the same equilibrium condition. The sorption curve (y-axis: Weight—% change vs. x-axis: % RH) is depicted in FIG. 3(a).

Example 17

Figure 3B:
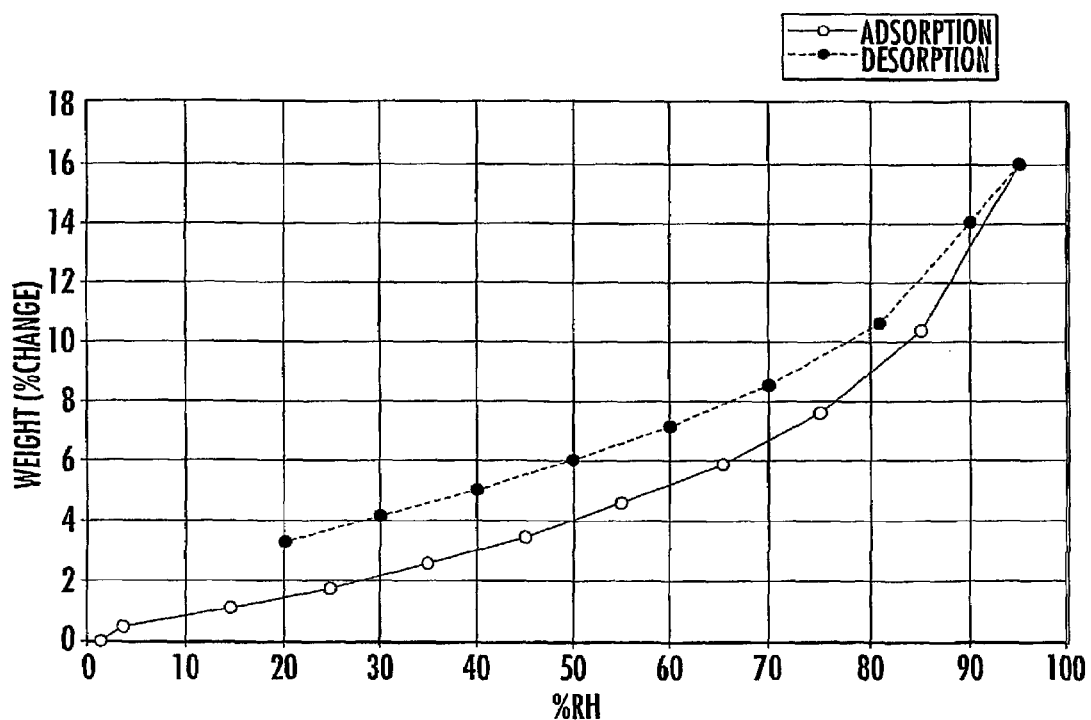
Figure 4:
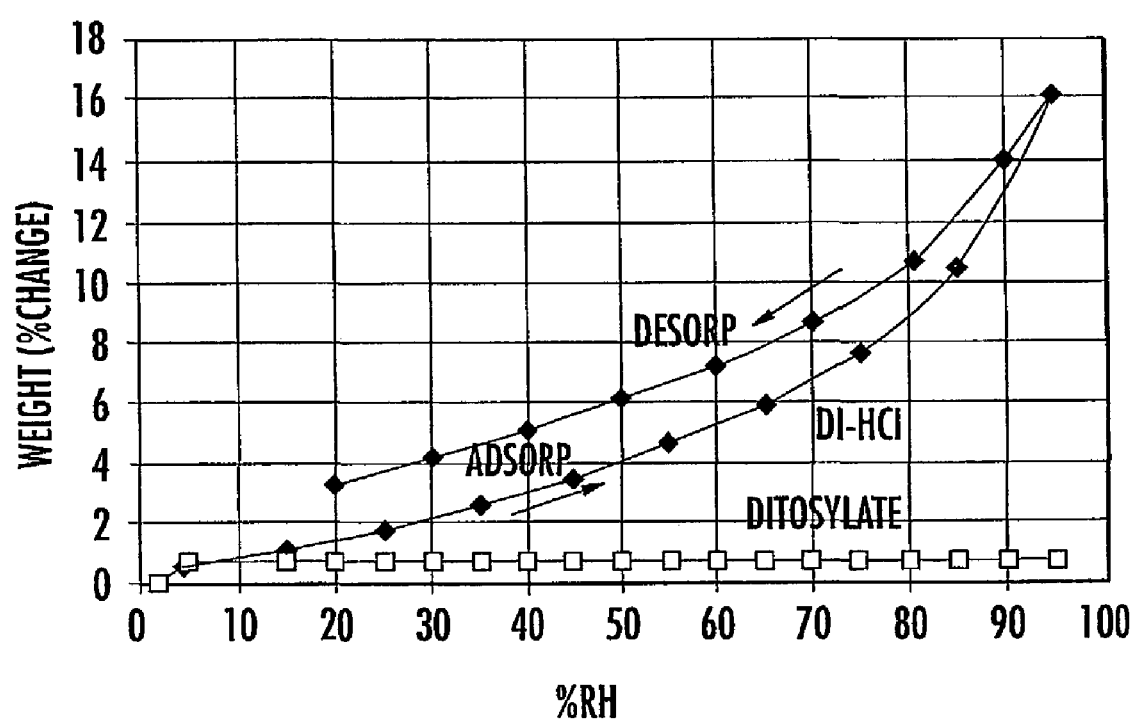
FIG. 4 depicts a comparison of the water sorption curves of N-{3-Chloro-4-[(3-fluorobenzyl) oxy]phenyl}-6-[5-({[2-(methanesulphonyl)ethyl]amino}methyl)-2-furyl]-4-quinazolinamine monohydrate ditosylate and di-HCl salts.

Moisture Sorption Testing N-{3-Chloro-4-[(3-fluorobenzyl) oxy]phenyl}-6-[5-({[2-(methanesulphonyl)ethyl]amino}methyl)-2-furyl]-4-quinazolinamine di-HCl salt Approximately 15 mg of N-{3-Chloro-4-[(3-fluorobenzyl) oxy]phenyl}-6-[5-({[2-(methanesulphonyl)ethyl] amino}methyl)-2-furyl]-4-quinazolinamine di-HCl salt was weighed into a sample pan of a moisture sorption apparatus (model number SGA-100, made by VTI). The sample was dried at 60° C. under a nitrogen stream until the weight loss was less than 0.015% in 5 minutes. The relative humidity was then increased (adsorption) to 5, 15, 25, 35, 45, 55, 65, 75, 85 and 95%—at each step, equilibrium was defined as a weight change of less than 0.015% in 5 minutes. The relative humidity was then decreased (desorption) to 90, 80, 70, 60, 50, 40, 30, and 20% with the same equilibrium condition. The sorption curve (y-axis: Weight—% change vs. x-axis: % RH) is depicted in FIG. 3(b).

Example 18

Relative Physical Stability of N-{3-Chloro-4-[(3-fluorobenzyl) oxy]phenyl}-6-[5-({[2-(methanesulphonyl)ethyl]amino}methyl)-2-furyl]-4-quinazolinamine ditosylate anhydrate and Monohydrate Crystal Forms A slurry equilibration method was used to determine the relative physical stability of N-{3-Chloro-4-[(3-fluorobenzyl) oxy]phenyl}-6-[5-({[2-(methanesulphonyl)ethyl] amino}methyl)-2-furyl]-4-quinazolinamine ditosylate anhydrate and monohydrate crystal forms. The method involved preparation of organic/aqueous slurries of known water activity containing mixtures of the anhydrate and monohydrate forms. The slurries equilibrated to the lowest free energy form, from which the relative physical stability was determined as a function of relative humidity.

Methanol (MeOH)/H$_2$O mixtures were prepared by volume and composition was converted to mole fraction ($X_w$) using molecular weights and room temperature densities (0.787 g/mL for MeOH and 1.00 g/mL for H$_2$O). Water activity ($a_w$) was calculated from:

$$a_w = 0.0056 + 1.398 X_w - 0.647 X_w^2 + 0.153 X_w^3 + 0.0845 X_w^4$$

(Zhu, H., Yuen, C., Grant, D. J. W., 1996. Influence of water activity in organic solvent+water mixtures on the nature of the crystallizing drug phase. 1. Theophylline. Int. J. Pharm. 135, 151–160.)

A 1:1 ratio of both crystal forms was added to vials and reconstituted with the MeOH/H$_2$O mixtures. After initial mixing, an aliquot was removed and dispensed for analysis by powder X-ray diffraction (model PADV, Scintag, Cupertino, Calif.) to ensure that peaks of both crystal forms were detectable. Samples were stirred and equilibrated at 25° C. in a water bath.

Figure 5:
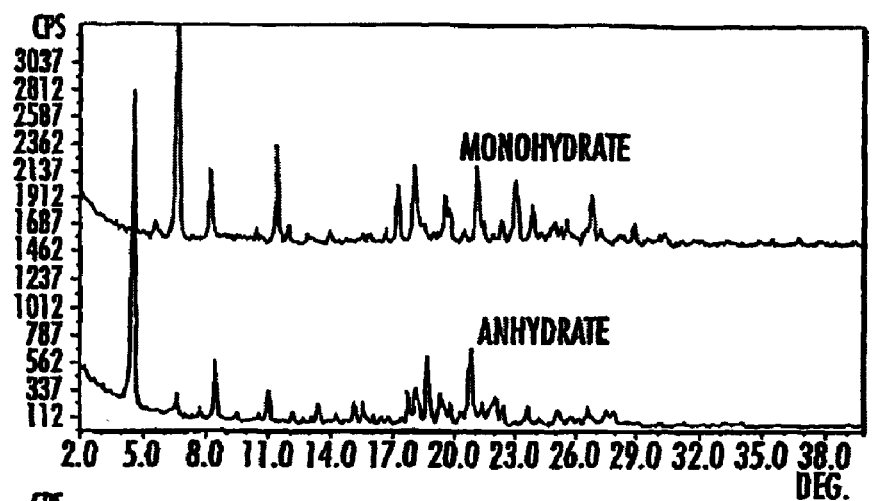
FIG. 5 depicts the powder X-ray diffraction patterns for N-{3-Chloro-4-[(3-fluorobenzyl) oxy]phenyl}-6-[5-({[2-(methanesulphonyl)ethyl]amino}methyl)-2-furyl]-4-quinazolinamine anhydrate and monohydrate crystal forms before and after stability testing. The top panel shows the patterns for the pure crystal forms. The middle panel shows the initial and 1 day results for a slurry with water activity equivalent to 70% RH. The bottom panel shows the initial and 1 day results for a slurry with water activity equivalent to 15% RH.
Figure 5:
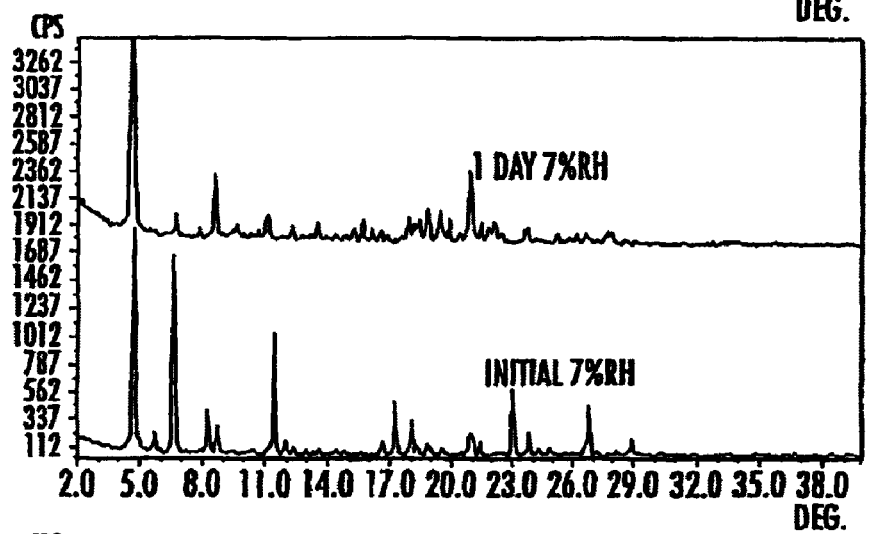
Figure 5:
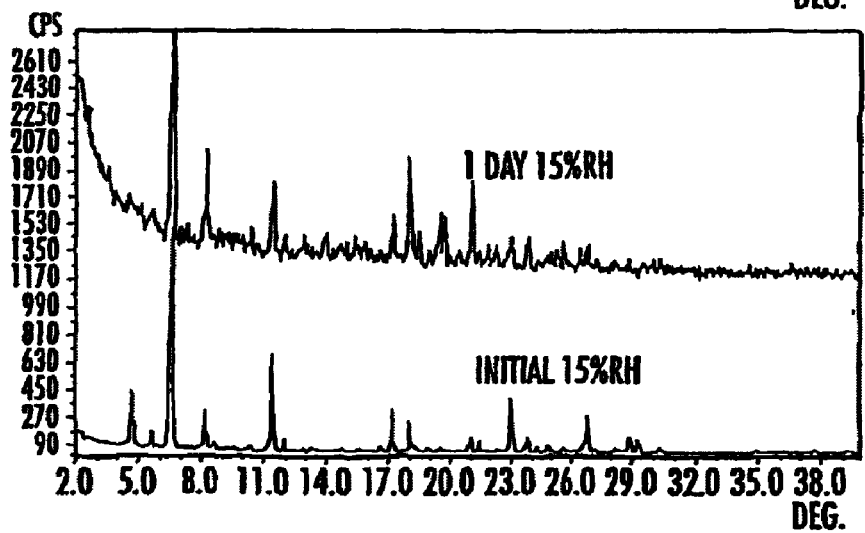

The results in Table III illustrate the crystal form conversion pattern as a function of calculated water activity/RH. The transformation rate was very rapid, as observed by powder X-ray diffraction (pXRD), not changing from the 1 day timepoint onward. The pXRD patterns are provided in FIG. 5. The top panel shows the results for the pure crystal forms of the anhydrate and monohydrate. The middle panel illustrates that the 1:1 mixture converted to the anhydrate in the liquid phase with a water activity equivalent to 7% RH. Likewise, the bottom panel demonstrates that the monohydrate is the stable form at a water activity equivalent to 15% RH. The summary in Table III notes that in general, the monohydrate becomes the thermodynamically stable form somewhere between 7–15% RH and remains stable up through 100% RH.

TABLE III

| Water Volume (%) | Water Mole Fraction | RH (%) | Equilibrium Form |
|---|---|---|---|
| 0 | 0.00 | 0 | Anhydrate |
| 2 | 0.04 | 7 | Anhydrate |
| 5 | 0.11 | 15 | Monohydrate |
| 10 | 0.20 | 26 | Monohydrate |
| 20 | 0.36 | 43 | Monohydrate |
| 40 | 0.60 | 66 | Monohydrate |
| 60 | 0.77 | 80 | Monohydrate |
| 80 | 0.90 | 91 | Monohydrate |
| 90 | 0.95 | 95 | Monohydrate |
| 100 | 1.00 | 100 | Monohydrate |

Biological Data

Compounds of the present invention were tested for erbB family protein tyrosine kinase inhibitory activity in substrate phosphorylation assays and cell proliferation assays.

Substrate Phosphorylation Assay

The substrate phosphorylation assays use baculovirus expressed, recombinant constructs of the intracellular domains of c-erbB-2 and c-erbB-4 that are constitutively active and EGFr isolated from solubilised A431 cell membranes. The method measures the ability of the isolated enzymes to catalyse the transfer of the g-phosphate from ATP onto tyrosine residues in a biotinylated synthetic peptide (Biotin-GluGluGluGluTyrPheGluLeuVal). Substrate phosphorylation was detected following either of the following two procedures:

a.) c-ErbB-2, e-ErbB4 or EGFr were incubated for 30 minutes, at room temperature, with 10 mM $MnCl_2$, 10 mM ATP, 5 mM peptide, and test compound (diluted from a 5 mM stock in DMSO, final DMSO concentration is 2%) in 40 mM HEPES buffer, pH 7.4. The reaction was stopped by the addition of EDTA (final concentration 0.15 mM) and a sample was transferred to a streptavidin-coated 96-well plate. The plate was washed and the level of phosphotyrosine on the peptide was determined using a Europium-labelled antiphosphotyrosine antibody and quantified with a time-resolved fluorescence technique.

b.) ErbB2 was incubated for 50 minutes at room temperature with 15 mM MnCl2, 2 mM ATP, 0.25 mCi [g-$^{33}$P] ATP/well, 5 mM peptide substrate, and test compound (diluted from a 10 mM stock in DMSO, final DMSO concentration is 2%) in. 50 mM MOPS pH 7.2. The reaction was terminated by the addition of 200 ml of PBS containing 2.5 mg/ml streptavidin-coated SPA beads (Amersham Inc.), 50 mM ATP, 10 mM EDTA and 0.10% TX-100. The microtitre plates were sealed and SPA beads were allowed to settle for at least six hours. The SPA signal was measured using a Packard Topeount 96-well plate scintillation counter (Packard Instrument Co., Meriden, Conn.).

The compounds tested were the products of Examples 8, 12, and 13, in buffered solution as indicated. Representative results are shown in Table IV for EGFR, erbB2, and erbB4 tyrosine kinase inhibition. Also, structures for the free base of the salts of Examples 8, 12, and 13 are given.

TABLE IV

| Example # | Structure | EGFR | ErbB2 | ErbB4 |
|---|---|---|---|---|
| 8 | 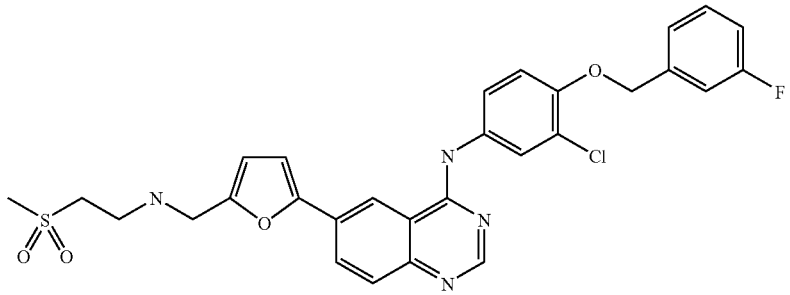 | +++ | +++ | ++ |
| 12 | 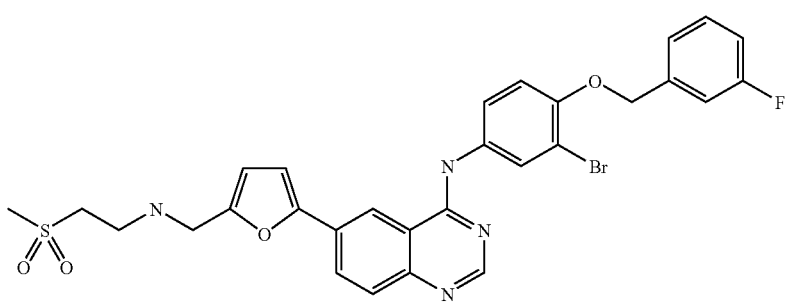 | +++ | +++ | ++ |

TABLE IV-continued

| Example # | Structure | EGFR | ErbB2 | ErbB4 |
|---|---|---|---|---|
| 13 | (structure) | +++ | +++ | + |

| IC$_{50}$ values | Symbol |
|---|---|
| <0.10 uM | +++ |
| 0.10–1.0 uM | ++ |
| 1.0–10.0 uM | + |
| >10.0 uM | – |
| Not determined | ND |

Cellular Assays: Methylene Blue Growth Inhibition Assay

Human breast (BT474), head and neck (HN5) and gastric tumor (N87) cell lines and human foreskin Fibroblasts (HFF) were cultured in low glucose DMEM (Life Technologies 12320-032) containing 10% fetal bovine serum (FBS) at 37° C. in a humidified 10% $CO_2$, 90% air incubator. The SV40 transformed human mammary epithelial cell line HB4a was transfected with either human H-ras cDNA (HB4a r4.2) or the human c-erbB2 cDNA (HB4a c5.2). The HB4a clones were cultured in RPMI containing 10% FBS, insulin (5 μg/ml), hydrocortisone (5 μg/ml), supplemented with the selection agent hygromycin B (50 μg/ml). Cells were harvested using trypsin/EDTA, counted using a haemocytometer, and plated in 100 ml of the appropriate media, at the following densities, in a 96-well tissue culture plate (Falcon 3075): BT474 10,000 cells/well, HN5 3,000 cells/well, N87 10,000 cells/well, HB4a c5.2 3,000 cells/well, HB4a r4.2 3,000 cells/well, HFF 2500 cells/well. The next day, compounds were diluted in DMEM containing 100 mg/ml gentamicin, at twice the final required concentration, from 10 mM stock solutions in DMSO. 100 ml/well of these dilutions were added to the 100 ml of media currently on the cell plates. Medium containing 0.6% DMSO was added to control wells. Compounds diluted in DMEM were added to all cell lines, including the HB4a r4.2 and HB4a c5.2 cell lines. The final concentration of DMSO in all wells was 0.3%. Cells were incubated at 37° C., 10% $CO_2$ for 3 days. Medium was removed by aspiration. Cell biomass was estimated by staining cells with 100 μl per well methylene blue (Sigma M9140, 0.5% in 50:50 ethanol:water), and incubation at room temperature for at least 30 minutes. Stain was removed, and the plates rinsed under a gentle stream of water, and air-dried. To release stain from the cells 100 μl of solubilization solution was added (1% N-lauroyl sarcosine, Sodium salt, Sigma L5125, in PBS), and plates were shaken gently for about 30 minutes. Optical density at 620 nM was measured on a microplate reader. Percent inhibition of cell growth was calculated relative to vehicle treated control wells. Concentration of compound that inhibits 50% of cell growth (IC$_{50}$) was interpolated using nonlinear regression (Levenberg-Marquardt) and the equation, $y = V_{max} \ast (1-(x/(K+x))) + Y2$, where "K" was equal to the IC$_{50}$.

Table V illustrates the inhibitory activity of compounds of the present invention as IC$_{50}$ values in μM against a range of tumor cell lines. Using HFF as a representative human normal cell line, values for cytotoxicity are supplied as IC50 values in micromolar. A measure of selectivity between normal and tumor lines is provided as well.

TABLE V

| Example # | N87 IC$_{50}$ uM Cell | BT474 IC$_{50}$ uM Cell | HN5 IC$_{50}$ uM Cell |
|---|---|---|---|
| 8 | +++ | +++ | +++ |
| 12 | +++ | +++ | +++ |
| 13 | +++ | +++ | +++ |

| IC$_{50}$ value | Symbol |
|---|---|
| <5 μM | +++ |
| 5–25 μM | ++ |
| 25–50 μM | + |
| >50 μM | – |
| Not determined | ND |

The invention claimed is:
1. A compound of Formula (II),

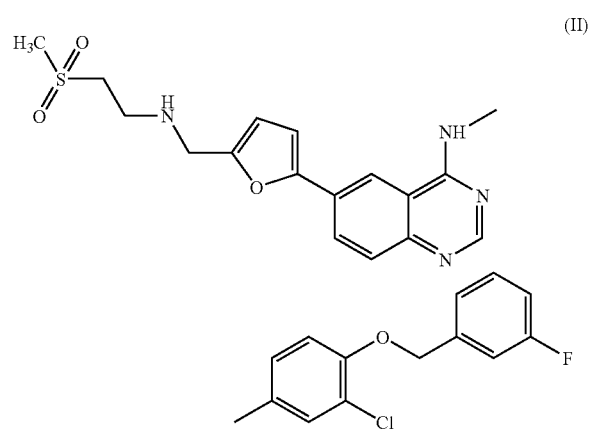

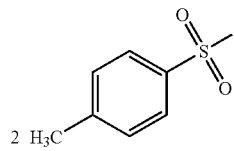

or anhydrate or hydrate forms thereof.

2. The compound of claim 1, wherein the compound is characterized by a powder x-ray diffraction pattern, comprising the peaks:

| Two theta (deg) | d-spacing (angstroms) |
|---|---|
| 4.8 | 18 |
| 8.7 | 10 |
| 18.0 | 4.9 |
| 18.9 | 4.7 |</p>

| Two theta (deg) | d-spacing (angstroms) |
|---|---|
| 21.0 | 4.2 |
| 22.3 | 4.0. |

3. The compound of claim 1, wherein the compound is characterized by a powder x-ray diffraction pattern, comprising the peaks:

| Two theta (deg) | d-spacing (angstroms) |
|---|---|
| 6.6 | 13 |
| 8.3 | 10 |
| 11.5 | 7.7 |
| 18.1 | 4.9 |
| 21.1 | 4.2. |

4. A compound of Formula (II),

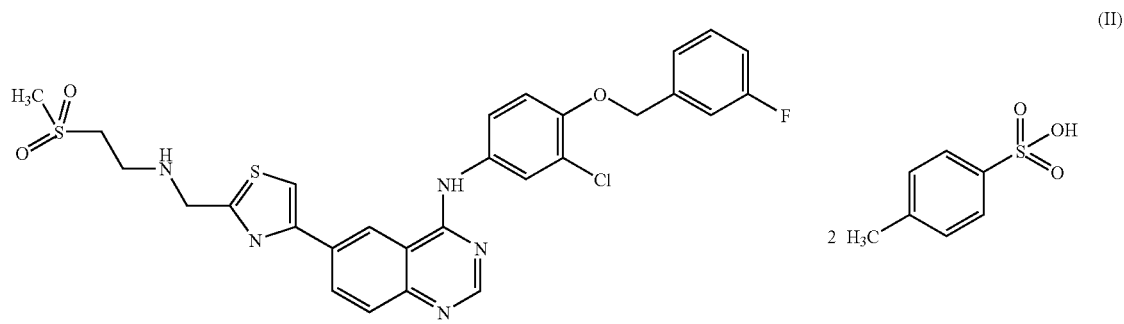

in anhydrate form.

5. A compound of Formula (II),

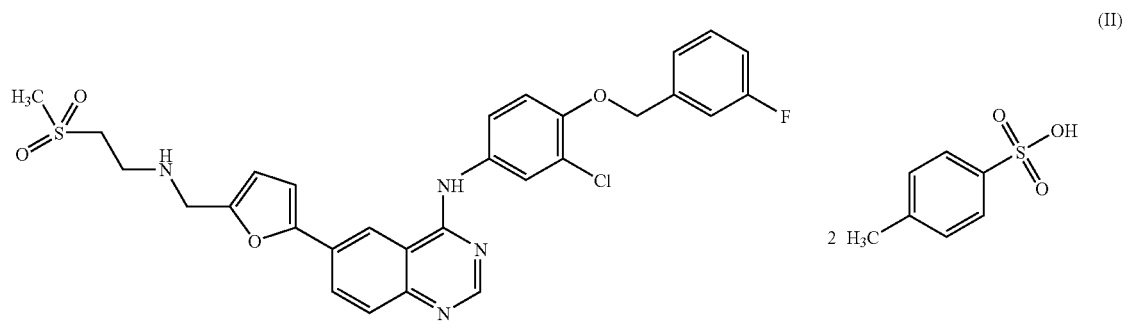

in monohydrate form.-

6. A mixture of anhydrous and hydrate forms of a compound of Formula (II),

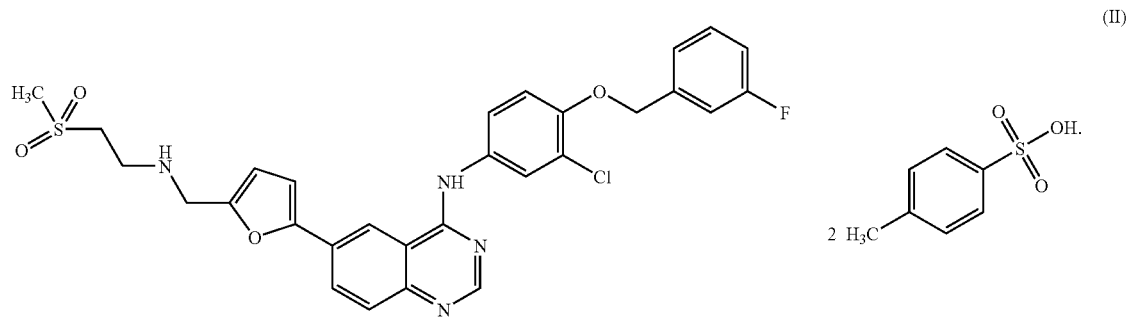

(II)

7. A pharmaceutical composition, comprising:
a therapeutically effective amount of a compound, or anhydrate or hydrate forms thereof, as claimed in claim 1 and one or m&re of pharmaceutically acceptable carriers, diluents and excipients.

8. A pharmaceutical composition, comprising:
a therapeutically effective amount of a compound, or anhydrate or hydrate forms thereof, as claimed in claim 4 and one or more of phamaceutically acceptable carriers, diluents and excipients.

9. A pharmaceutical composition, comprising:
a therapeutically effective amount of a compound, or anhydrate or hydrate forms thereof, as claimed in claim 5 and one or more of pharmaceutically acceptable carriers, diluents and excipients.

10. A pharmaceutical composition, comprising:
a therapeutically effective amount of the mixture, as claimed in claim 6 and one or more of pharmaceutically acceptable carriers, diluents and excipients.

* * * * *

UNITED STATES PATENT AND TRADEMARK OFFICE
CERTIFICATE OF CORRECTION

PATENT NO. : 7,157,466 B2
APPLICATION NO. : 10/311678
DATED : January 2, 2007
INVENTOR(S) : McClure et al.

It is certified that error appears in the above-identified patent and that said Letters Patent is hereby corrected as shown below:

On Title page item 75 should be deleted: "Martin Howard Osterhout, Durham NC (US); Frank Roschangar, Glenn Allen, VA (US);"

Column 4, line 34, --ditosylate-- should be inserted between "quinazolinamine" and "anhydrate".

The formula of the last compound shown in columns 13 and 14 should read as follows:

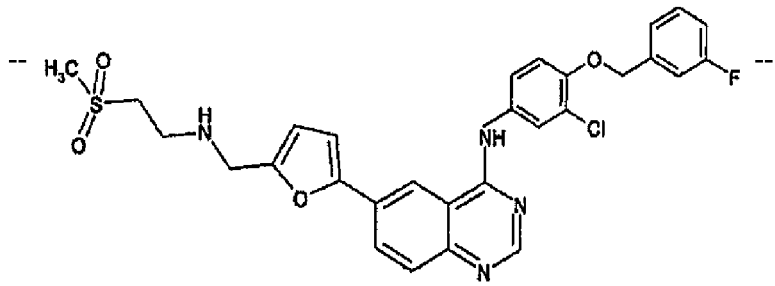

Column 21, line 43 "NRR'" should be replaced with --NR'R"--

In claim 1, Formula (II) should read as follows:

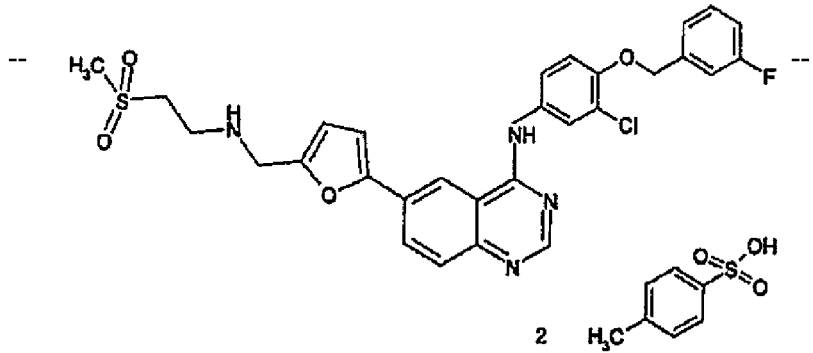

UNITED STATES PATENT AND TRADEMARK OFFICE
CERTIFICATE OF CORRECTION

PATENT NO. : 7,157,466 B2
APPLICATION NO. : 10/311678
DATED : January 2, 2007
INVENTOR(S) : McClure et al.

It is certified that error appears in the above-identified patent and that said Letters Patent is hereby corrected as shown below:

In claim 4, Formula (II) should read as follows:

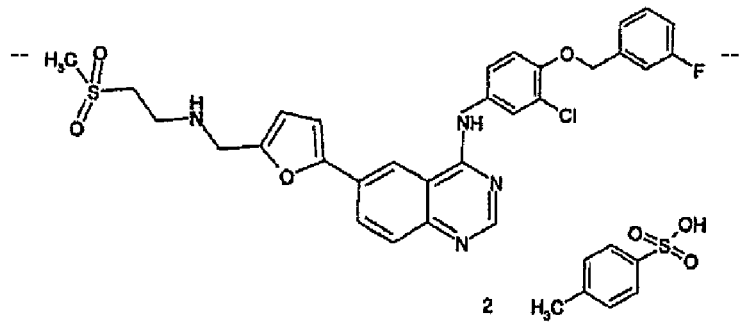

Column 43, line 23 (claim 7), "m&re" should be replaced with --more--.

Column 43, lines 26-27 (claim 8), "a compound, or anhydrate or hydrate forms thereof," should be replaced with -- an anhydrate form of a compound of Formula (II)--

Column 44, lines 21-22 (claim 9), "a compound, anhydrate or hydrate forms thereof," should be replaced with -- a monohydrate form of a compound of Formula (II)--

Signed and Sealed this

Twenty-second Day of May, 2007

JON W. DUDAS
*Director of the United States Patent and Trademark Office*

UNITED STATES PATENT AND TRADEMARK OFFICE
Certificate

Patent No. 7,157,466 B2            Patented: January 2, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael Scott McClure, Durham, NC (US); Mark Joseph Sacchetti, Foster City, CA (US); and Martin Howard Osterhout, Durham, NC (US).

Signed and Sealed this Fifteenth Day of April 2014.

EMILY BERNHARDT
*Supervisory Patent Examiner*
Art Unit 1624
Technology Center 1600

UNITED STATES PATENT AND TRADEMARK OFFICE
Certificate

Patent No. 7,157,466 B2                                                          Patented: January 2, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael Scott McClure, Durham, NC (US); Mark Joseph Sacchetti, Foster City, CA (US); and Martin Howard Osterhout, Durham, NC (US).

Signed and Sealed this Thirteenth Day of May 2014.

<div style="text-align:right">
JAMES WILSON<br>
<em>Supervisory Patent Examiner</em><br>
Art Unit 1624<br>
Technology Center 1600
</div>